(12) United States Patent
Bodduluri et al.

(10) Patent No.: US 9,913,610 B2
(45) Date of Patent: Mar. 13, 2018

(54) SYSTEMS AND METHODS FOR SELECTING A DESIRED QUANTITY OF FOLLICULAR UNITS

(71) Applicant: Restoration Robotics, Inc., San Jose, CA (US)

(72) Inventors: Mohan Bodduluri, Palo Alto, CA (US); Gabriele Zingaretti, Capitola, CA (US)

(73) Assignee: RESTORATION ROBOTICS, INC., San Jose, CA (US)

( * ) Notice: Subject to any disclaimer, the term of this patent is extended or adjusted under 35 U.S.C. 154(b) by 453 days.

(21) Appl. No.: 14/574,066

(22) Filed: Dec. 17, 2014

(65) Prior Publication Data

US 2015/0112204 A1    Apr. 23, 2015

Related U.S. Application Data

(62) Division of application No. 13/110,820, filed on May 18, 2011, now Pat. No. 8,945,150.

(51) Int. Cl.
*A61B 17/50* (2006.01)
*A61B 5/00* (2006.01)
(Continued)

(52) U.S. Cl.
CPC ............ *A61B 5/448* (2013.01); *A61B 5/0077* (2013.01); *A61B 5/1072* (2013.01);
(Continued)

(58) Field of Classification Search
CPC ..... A61B 5/448; A61B 5/0077; A61B 5/1072; A61B 5/1079; A61B 5/4836;
(Continued)

(56) References Cited

U.S. PATENT DOCUMENTS 4,807,163 A    2/1989  Gibbons
5,331,472 A    7/1994  Rassman
(Continued)

FOREIGN PATENT DOCUMENTS

CN    1589748 A    3/2005
CN    101128156 A    2/2008
(Continued)

OTHER PUBLICATIONS

English Translation of Office Action dated Feb. 17, 2015, in connection with commonly assigned Chinese Patent Application No. 201280022177.0, Feb. 17, 2015, (7 pages).
(Continued)

*Primary Examiner* — Ashley Fishback

(57) ABSTRACT

Systems and methods for selecting follicular units in a distribution of follicular units are provided. A selection parameter, such as a distance-related parameter separating the follicular units to be selected, may be used to determine a desired quantity of follicular units to be selected, such as a desired percentage of follicular units to be selected, and to help provide a substantially uniform distribution of selected follicular units. In addition, a characteristic parameter, such as a characteristic distance or characteristic density, may be determined. The characteristic parameter may be used in determining the desired quantity of follicular units to be selected and or may be used for treatment purposes.

20 Claims, 16 Drawing Sheets

(51) Int. Cl.

| | | |
|---|---|---|
| *A61F 2/10* | (2006.01) | |
| *G06T 7/00* | (2017.01) | |
| *A61B 5/107* | (2006.01) | |
| *A61B 17/322* | (2006.01) | |
| *G06F 17/18* | (2006.01) | |
| *A61B 34/30* | (2016.01) | |
| *A61B 34/10* | (2016.01) | |
| *A61B 17/00* | (2006.01) | |
| *A61B 90/50* | (2016.01) | |
| *A61B 90/00* | (2016.01) | |

(52) U.S. Cl.
CPC .......... *A61B 5/1079* (2013.01); *A61B 5/4836* (2013.01); *A61B 5/7203* (2013.01); *A61B 5/7278* (2013.01); *A61B 5/7425* (2013.01); *A61B 5/7475* (2013.01); *A61B 17/322* (2013.01); *A61B 34/10* (2016.02); *A61B 34/30* (2016.02); *A61F 2/10* (2013.01); *G06F 17/18* (2013.01); *G06T 7/0012* (2013.01); *A61B 2017/00752* (2013.01); *A61B 2034/108* (2016.02); *A61B 2090/3612* (2016.02); *A61B 2090/502* (2016.02); *A61B 2576/02* (2013.01); *G06T 2207/30088* (2013.01); *G06T 2207/30242* (2013.01)

(58) Field of Classification Search
CPC .................. A61B 5/7425; A61B 34/10; A61B 2017/00752; A61B 2034/108; A61B 2576/02; G06T 7/0012; G06T 7/0014; G06T 2207/30088; G06T 2207/30242
See application file for complete search history.

(56) References Cited

U.S. PATENT DOCUMENTS

| | | | |
|---|---|---|---|
| 5,584,581 | A | 12/1996 | Banuchi |
| 5,951,572 | A | 9/1999 | Markman |
| 6,572,625 | B1 | 6/2003 | Rassman |
| 6,585,746 | B2 | 7/2003 | Gildenberg |
| 6,949,115 | B2 | 9/2005 | Mascio |
| 7,127,081 | B1 | 10/2006 | Erdem |
| 7,217,266 | B2 | 5/2007 | Anderson et al. |
| 7,477,782 | B2 | 1/2009 | Qureshi et al. |
| 7,627,157 | B2 | 12/2009 | Qureshi et al. |
| 2001/0015380 | A1 | 8/2001 | Good et al. |
| 2004/0193203 | A1 | 9/2004 | Pak et al. |
| 2006/0089555 | A1 | 4/2006 | Gummer et al. |
| 2006/0127881 | A1 | 6/2006 | Wong et al. |
| 2007/0078466 | A1 | 4/2007 | Bodduluri et al. |
| 2007/0150247 | A1 | 6/2007 | Bodduluri |
| 2008/0033455 | A1 | 2/2008 | Rassman et al. |
| 2008/0140198 | A1 | 6/2008 | Unger |
| 2008/0216334 | A1 | 9/2008 | Pak et al. |
| 2009/0036800 | A1 | 2/2009 | Rabin et al. |
| 2009/0052738 | A1 | 2/2009 | Qureshi et al. |
| 2009/0306498 | A1 | 12/2009 | Bodduluri et al. |
| 2009/0306680 | A1 | 12/2009 | Qureshi et al. |
| 2010/0234871 | A1 | 9/2010 | Qureshi et al. |

FOREIGN PATENT DOCUMENTS

| | | |
|---|---|---|
| CN | 101277657 A | 10/2008 |
| CN | 101505659 A | 8/2009 |
| CN | 101506825 A | 8/2009 |
| CN | 1318992 A | 10/2009 |
| WO | WO 2000/064379 | 11/2000 |
| WO | WO 2003/044737 | 5/2003 |
| WO | WO 2007/041267 | 4/2007 |
| WO | WO 2008/024954 | 2/2008 |
| WO | WO 2008/024955 | 2/2008 |
| WO | WO2009146068 A1 | 12/2009 |
| WO | WO2011035125 A1 | 3/2011 |

OTHER PUBLICATIONS

PCT Int'l Search Report and Written Opinion Forms PCT/ISA/220, PCT/ISA/237 in relation to commonly assigned PCT Application No. PCT/US2012/036737, dated Nov. 23, 2012. Applicant Restoration Robotics, Inc. (12 pages).

Alhaddab, et al., "Effect of Graft Size, Angle, and Intergraft Distance on Dense Packing in Hair Transplant", Dermatol Surg. 31:6, Jun. 2005, 650-654.

Bernstein, et al., "Follicular Transplantation", International Journal of Aesthetic and Restorative Surgery. vol. 3, No. 2., 1995, 119-132.

Bernstein, et al., "The Logic of Follicular Unit Transplantation", Dermatologic Clinics vol. 17, No. 2,, Apr. 1999, 277-296.

Canfield, "Photographic Documentation of Hair Growth in Androgenetic Alopecia", Dermatologic Clinics vol. 14, No. 4, Oct. 1996, 713-721.

Hoffman, et al., "Recent Findings with Computerized Methods for Scalp Hair Growth Measurements", The Journal of investigative dermatology symposium proceedings 2005, vol. 10, No. 3, 2005, pp. 285-288.

Inaba, et al., "Androgenetic Alopecia, Modern Concepts of Pathogenesis and Treatment, 29. Operative Treatment for Androgenetic Alopecia.", 1996, pp. 238-244, 309 (9 pages).

Jimenez, et al., "Distribution of Human Hair in Follicluar Units—A Mathematical Model for Estimating the Donor Size in Follicular Unit Transplantation", Dermatol Surg. 25:4, Apr. 1999, 294-298.

Lee, et al., "New Instrument for Hair Transplant: Multichannel Hair Transplanter", Dermatol Surg 2005. 31:379, 2005, 1 page.

English Language Translation of Office Action dated Jan. 20, 2014, in connection with commonly assigned Korean Patent Application No. 10-2013-7030469 (2 pages).

SYSTEMS AND METHODS FOR SELECTING A DESIRED QUANTITY OF FOLLICULAR UNITS

RELATED APPLICATION

The present application is a division of co-pending U.S. patent application Ser. No. 13/110,820, filed May 18, 2011 and entitled "Systems and Method for Selecting a Desired Quantity of Follicular Units".

TECHNICAL FIELD

The present disclosure generally relates to hair transplantation procedures, and in particular, to systems and methods for determining follicular units for use in hair transplantation procedures.

BACKGROUND INFORMATION

Hair transplantation procedures typically involve harvesting donor hair grafts and implanting them in a recipient area on a patient. The donor hair grafts are generally harvested from such areas as the back fringe or side areas of a donor's scalp, or other surfaces containing hair. Previously, harvested donor hair grafts were relatively large (3-5 mm). Recent attempts use smaller donor grafts consisting of single follicular units (also referred to as "FUs"), i.e., naturally occurring aggregates of 1-3 (and sometimes 4 or 5) closely spaced hair follicles randomly distributed over a body surface, such as a scalp.

Previous hair transplantation procedures include manual or mechanized procedures featuring some automation. In one manual process, a linear strip of scalp tissue having donor hair grafts is removed with a scalpel down into the fatty subcutaneous tissue. The component follicular units in the strip are then isolated and separated under a microscope. The follicular units are implanted into a recipient area in respective puncture holes made by a needle. Forceps are typically used to grasp and place the follicular units into the needle puncture locations, although other instruments and methods may be used. In an alternative manual process called follicular unit extraction, a hand-held punch or cannula is used to individually extract follicular units from a body surface for subsequent implantation in another location.

Follicular units may be classified based on the number of hair follicles in the unit. For example, an "F1" is a shorthand designation for a follicular unit with a single hair; an "F2" designates a two-hair follicular unit, and so on for F3s, F4s, or follicular units with higher numbers of hair follicles. The distance between a follicular unit and another follicular unit is generally referred to as an interfollicular-unit distance. Specific classes or types of follicular units may be transplanted into specific regions of a scalp. For example, F1s may be implanted along a hairline framing face. Multiple hair follicular units, e.g., F2s, F3s, or greater, are preferably implanted in mid-scalp and crown regions.

A doctor or patient may prefer to harvest only a desired percentage of follicular units and leave some coverage in a donor area. Moreover, a doctor or patient may prefer to evenly distribute the desired percentage amongst remaining follicular units to avoid over-thinning or under-thinning areas of the donor area. However, obtaining an appropriate selection is difficult due to the relatively small size and high number of follicular units, in conjunction with pre-harvested follicular units, image artifacts, occlusion caused by blood or tissue damage, or other discrepancies within the donor area.

SUMMARY

According to one embodiment, a method for determining a desired quantity of follicular units to be selected in a distribution of follicular units is provided. The method includes determining, with a processor, a quantity of follicular units to be selected in the distribution of follicular units based on a value of a selection parameter and iteratively selecting a different value as the value of the selection parameter and repeating the determining step until the value of the selection parameter yields the desired quantity of follicular units to be selected in the distribution of follicular units. According to one embodiment, the selection parameter comprises a selection distance. In certain embodiments the method comprises selecting a first distance as a selection distance to be used for selecting follicular units in a distribution of follicular units; determining, with a processor, a quantity of follicular units to be selected in the distribution of follicular units based on the selection distance; and iteratively selecting a different distance as the selection distance and repeating the determining step until the selection distance yields a desired quantity of follicular units to be selected in the distribution of follicular units.

In another embodiment, a system for determining a desired quantity of follicular units to be selected in a distribution of follicular units is provided. Such system may comprise means for determining a quantity of follicular units to be selected in the distribution of follicular units based on a value of a selection parameter, and means for iteratively selecting a different value as the value of the selection parameter and determining the quantity of follicular units to be selected based on the value of the selection parameter until the value of the selection parameter yields the desired quantity of follicular units to be selected in the distribution of follicular units. In certain embodiments, a selection parameter may be a distance-related selection parameter and the system may further comprise means for selecting a first value of the distance-related parameter to be used for selecting follicular units in a distribution of follicular units.

In still another embodiment, a computer readable medium has instructions stored thereon for determining a desired quantity of follicular units to be selected in a distribution of follicular units. The instructions include instructions for determining a quantity of follicular units to be selected in the distribution of follicular units based on a value of a selection parameter, and instructions for iteratively selecting a different value as the value of the selection parameter and determining the quantity of follicular units to be selected based on the value of the selection parameter until the value of the selection parameter yields the desired quantity of follicular units to be selected in the distribution of follicular units.

In yet another embodiment, a system comprises an interface configured to receive follicular unit distribution data reflecting locations of follicular units on a body surface, and a processor operatively coupled to the interface. The processor is configured to determine a quantity of follicular units to be selected based on a value of a selection parameter and the follicular unit distribution data, and iteratively select a different value as the value of the selection parameter and determine the quantity of follicular units to be selected based on the value of the selection parameter and the follicular unit distribution data until the value of the selection parameter yields the desired quantity of follicular units to be selected. The processor may be further configured to select a first value of the selection parameter (e.g. distance-related parameter) to be used for selecting follicular units from the follicular unit distribution data.

In still another embodiment, a method is provided including selecting a distance, determining based on follicular unit distribution data and with a processor, a quantity of follicular units separated by at least the selected distance, and repeating the selecting and determining steps until a desired quantity of follicular units is determined.

In yet another embodiment, a method for selecting follicular units from follicular unit distribution data comprises (a) selecting first and second distances having associated therewith corresponding first and second quantities of follicular units such that the first quantity is greater than a desired quantity of follicular units and the second quantity is less than the desired quantity, (b) choosing with a processor an iterator distance having a value in a range between the first and second distances, (c) determining based on the follicular unit distribution data a resulting quantity of follicular units corresponding to the iterator distance, (d) comparing the resulting quantity to the desired quantity to determine whether the resulting quantity is greater than, less than, or within an acceptable tolerance of the desired quantity, (e) adapting at least one of the first or second distances based on whether the resulting quantity is greater than or less than the desired quantity, and (f) repeating the choosing, determining, comparing, and adapting steps until it is determined that the resulting quantity is within the acceptable tolerance of the desired quantity.

The step of selecting the first and second distances may further comprise (a) generating a statistical distribution for a set of follicular units, wherein the statistical distribution has a set of mean interfollicular-unit distances, (b) for individual mean interfollicular-unit distances in the set, determining based on the follicular unit distribution data a set of derived quantities of follicular units, such that individual derived quantities correspond to individual mean interfollicular-unit distances in the set, (c) identifying first and second derived quantities within the set of derived quantities such that the first quantity comprises the first derived quantity and the second quantity comprises the second derived quantity, (d) setting the first distance equal to a first mean distance associated with the first quantity, and (e) setting the second distance is set to equal to a second mean distance associated with the second quantity.

In an alternative embodiment, the step of selecting the first and second distances comprises (a) determining an average interfollicular-unit distance, (b) determining based on the follicular unit distribution data, a derived quantity of follicular units corresponding to the average interfollicular-unit distance, (c) comparing the derived quantity to the desired quantity to determine whether the derived quantity is greater than or less than the desired quantity, (d) if the desired quantity is less than the derived quantity, selecting the average interfollicular-unit distance as the first distance, and (e) if the desired quantity is greater than the derived quantity, selecting the average interfollicular-unit distance as the second distance.

In still another embodiment, a method of calculating a characteristic parameter of follicular units from follicular unit distribution data is provided. The method comprises, for a set of selected follicular units, calculating, with a processor, an average value of a parameter between a selected follicular unit and a set of closest neighboring follicular units to establish a set of average values, and calculating, with the processor, the characteristic parameter as the average of the set of average values. In one embodiment, the parameters are based on distance or distance-related.

In yet another embodiment, a system for calculating a characteristic parameter of follicular units from follicular unit distribution data comprises means for calculating, for a set of selected follicular units, an average value of a parameter between a selected follicular unit and a set of closest neighboring follicular units to establish a set of average values, and means for calculating the characteristic parameter as the average of the set of average values.

In still another embodiment, a computer readable medium has instructions stored thereon for calculating a characteristic parameter of follicular units from follicular unit distribution data. The instructions include instructions for a set of selected follicular units, an average value of a parameter between a selected follicular unit and a set of closest neighboring follicular units to establish a set of average values, and instructions for calculating a characteristic parameter as the average of the set of average values.

In yet another embodiment, a system comprises an interface configured to receive follicular unit distribution data reflecting locations of follicular units on a body surface, and a processor operatively coupled to the interface. The processor is configured to calculate, for a set of selected follicular units, an average value of a parameter between a selected follicular unit and a set of closest neighboring follicular units to establish a set of average values, and to calculate a characteristic parameter as the average of the set of average values.

In still another embodiment, a method of calculating a density of follicular units from an image of a body surface including follicular units, is provided. The method comprises, for a set of selected follicular units, calculating an average distance between a selected follicular unit and a set of closest neighboring follicular units to establish a set of average distances, calculating an average interfollicular-unit distance of the set of average distances, and converting the average interfollicular-unit distance into a density to establish an estimated density of the follicular units.

In yet another embodiment, a method comprises determining in a distribution of follicular units, an original hair density existing prior to some natural hair loss, harvesting procedure, or the original hair density existing but not accurately determinable due to undetectable hair, and using the determined original hair density for harvesting or implanting follicular units in the distribution of follicular units.

In still another embodiment, a method includes, for a set of selected follicular units in a distribution of follicular units, calculating, with a processor, an average value of a parameter between a selected follicular units and a set of closest neighboring follicular units to establish a set of average values, calculating an average of the set of average values to establish a characteristic parameter of follicular units, and selecting, based on the characteristic parameter or an original density derived therefrom, implantation sites on a body surface or follicular units to be harvested from the distribution of follicular units.

DETAILED DESCRIPTION OF EMBODIMENTS

With reference to the above-listed drawings, this section describes particular embodiments and their detailed construction and operation. The embodiments described herein are set forth by way of illustration only and not limitation. Those skilled in the art will recognize in light of the teachings herein that, for example, other embodiments are possible, variations can be made to the example embodiments described herein, and there may be equivalents to the components, parts, or steps that make up the described embodiments.

For the sake of clarity and conciseness, certain aspects of components or steps of certain embodiments are presented without undue detail where such detail would be apparent to skilled persons in light of the teachings herein and/or where such detail would obfuscate an understanding of more pertinent aspects of the embodiments.

One or more steps in the methods or procedures described herein may be automated, or autonomous, with some parts requiring manual input. An automated system may include some operator interaction such as activating an ON switch or scheduling an operation, or a system in which hand held tools are used but some mechanism of the system functions autonomously, i.e., without human input, to perform a function. Some of the automated systems described herein may also be robotically assisted or computer/software/machine-instruction controlled. The devices and methods described herein may be used in manual procedures and systems, as well as in automated procedures and system. An example robotically-assisted system and procedure is described with respect to FIG. 15.

Figure 1:
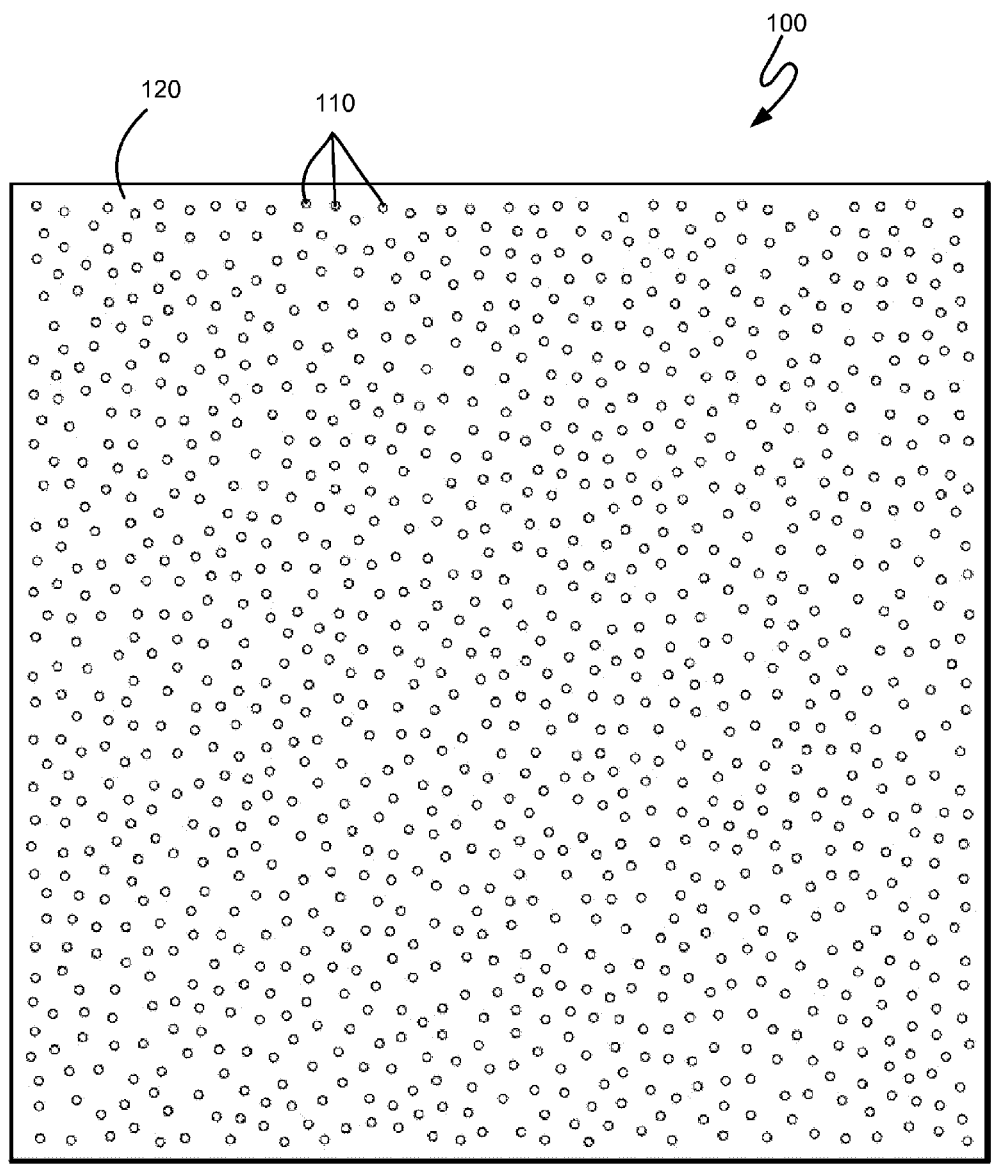
FIG. 1 is a diagram illustrating an example distribution of follicular units on a body surface.

FIG. 1 is a diagram illustrating a distribution 100 of follicular units 110 on a body surface 120. A distribution of follicular units is defined as a representation of a group of follicular units on a body surface. In FIG. 1, each dot represents a location of a follicular unit 110 on the body surface 120. The body surface 120 could be any area of a body having hair; a body surface can be attached to the body, or a flap of skin, or tissue removed from a body. The follicular unit distribution 100, may be obtained from image data captured by one or more imaging devices viewing, for example, a patient's scalp. The image data may be processed using suitable techniques to identify the locations of each of the follicular units. Alternatively, the follicular unit distribution 100 may be coordinate data of follicular unit locations obtained using measurement instruments manually or automatically.

Figure 2:
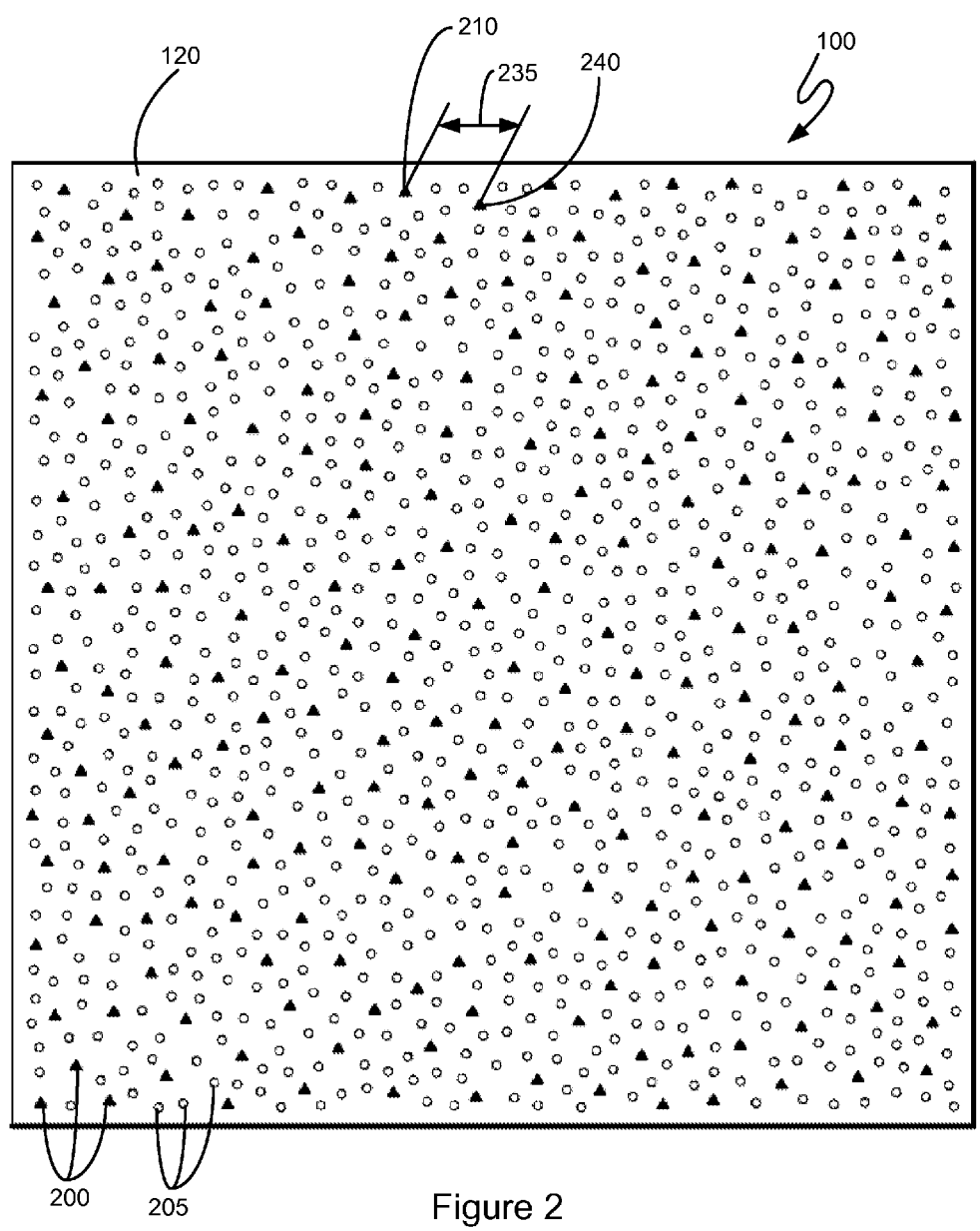
FIG. 2 is a diagram as in FIG. 1 illustrating a first desired quantity of follicular units to be selected from the distribution of follicular units based on a first selection distance, according to one embodiment.

FIG. 2 is a diagram as in FIG. 1 illustrating an example of a first desired quantity of follicular units to be selected (depicted as triangles 200) from the distribution 100 of follicular units based on a selection parameter (e.g., a value of a selection parameter) that represents a relationship between follicular units. In one embodiment, the value of the selection parameter comprises a distance between follicular units to be selected. Skilled persons will recognize that instead of pure distance, other distance-related parameters (including area-based, angle-based, distance-based, derivatives, functions, or metrics) or other combined parameters (one of which may relate, for example, to distance, area or an angle) between follicular units may be used as a selection parameter. For example, dot products (also known as scalar products), such as dot products of vectors generated between pairs of follicular units may be used as the selection parameter, i.e., the dot product is an example of a distance-related parameter. When describing various examples and referencing distances, it should be understood that distance is used as an example. The follicular units denoted by triangles represent, for example, follicular units identified for potential harvest or follicular units to be retained or reserved in a donor area (such as on the body surface 120) after a harvesting procedure. In FIG. 2, approximately 20% of the follicular units are denoted with triangles 200, which specify, for example, locations of follicular units to be harvested. Follicular units depicted as dots 205 denote, for example, follicular units that will be left behind on the donor area 120.

Figure 3:
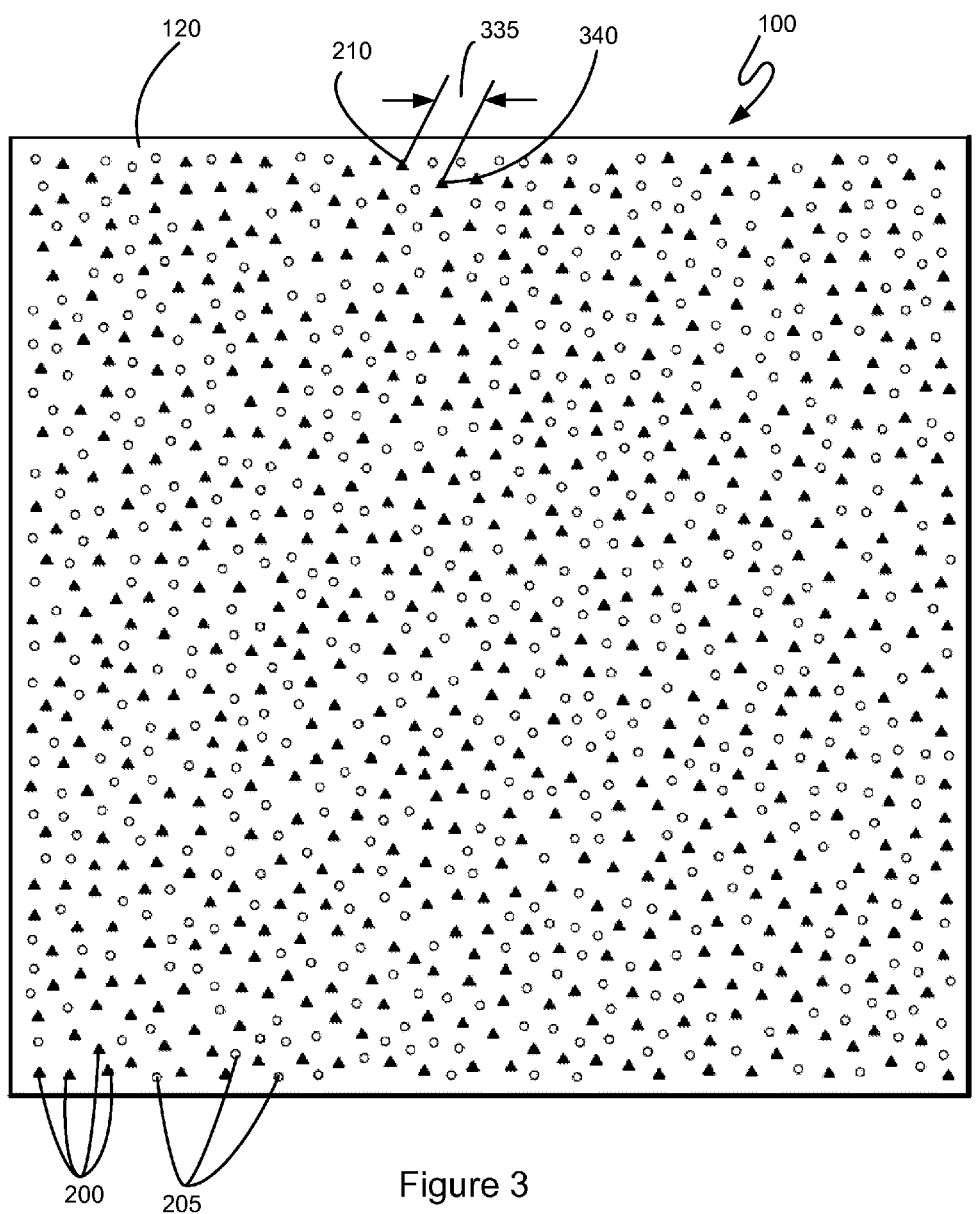
FIG. 3 is a diagram as in FIG. 1 illustrating a second desired quantity of follicular units to be selected from the distribution of follicular units based on a second selection distance that is less than the first selection distance, according to one embodiment.

FIG. 3 illustrates the follicular unit distribution 100 with follicular unit locations positioned as in FIGS. 1 and 2, but with approximately 50% of the follicular units selected. The selected follicular units 200 illustrated in FIGS. 2 and 3 are substantially uniformly distributed to help avoid excessive thinning or under-thinning in portions of the donor area 120.

The selected follicular units 200 may be selected according to the methods described with reference to FIGS. 4-7, 9, 11, 13, and/or 14.

FIGS. 2 and 3 show that an average interfollicular-unit distance between selected follicular units 200 decreases as the density of selected follicular units 200 increases. For example, a follicular unit 210 in FIG. 3 has closer adjacent selected follicular units than the corresponding follicular unit 210 in FIG. 2. In other words, an interfollicular-unit distance 235 between a follicular units 210 and a follicular unit 240 in FIG. 2 is greater than an interfollicular-unit distance 335 between the follicular units 210 and a follicular unit 340 in FIG. 3. A specified minimum distance between each harvest, implant, or retained location may be used to determine the density of selected follicular units while helping to provide a substantially uniform distribution of the selected follicular units. Similarly, a desired quantity (percentage, raw total number, or density equivalent) of follicular units to be harvested, implanted, or retained can be used to determine a minimum interfollicular-unit distance between selected follicular units. As described herein, any reference to a quantity (or set) of follicular units may imply either a raw number of follicular units, a percentage, or a density of follicular units.

Figure 4:
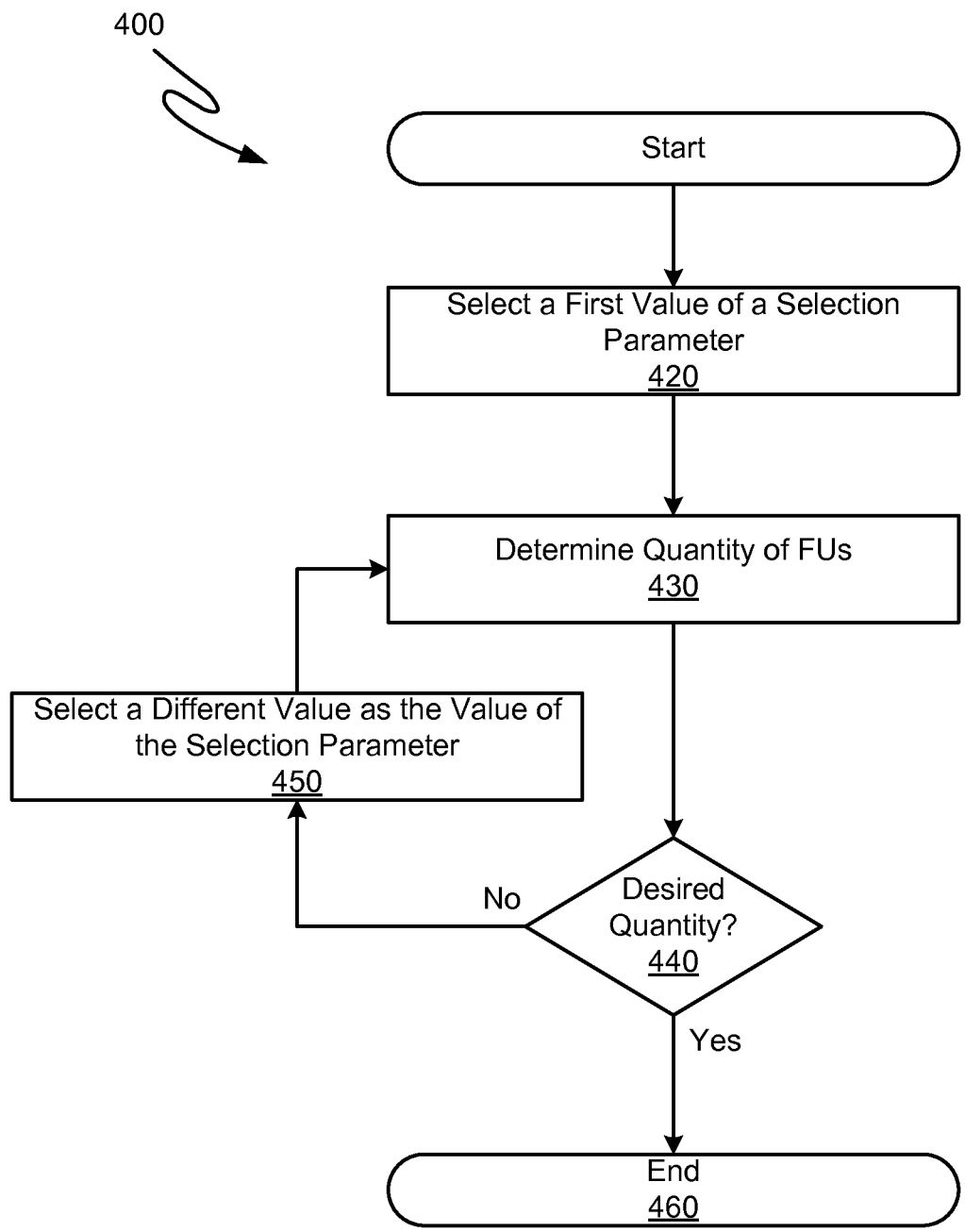
FIG. 4 is a flow diagram of a method of determining a desired quantity of follicular units to be selected in a distribution of follicular units, according to one embodiment.

FIG. 4 is a flow diagram of a method 400 of determining a desired quantity of follicular units to be selected in a distribution of follicular units, according to one embodiment. At an optional step 420, a first value of a selection parameter is selected. As discussed above, the selection parameter may be a selection distance, in which case the first value may be a first distance used as an initial selection distance for selecting follicular units in a distribution of follicular units. The first distance may be selected by a processor, control logic hardware, software, manually as described with reference to FIG. 16, or by other components described with reference to FIG. 15.

At step 430, a quantity of follicular units to be selected among the distribution of follicular units is determined, based on a value of a selection parameter. According to one embodiment, the selection parameter is a selection distance. The distribution may be determined from an image or a data set containing a set of locations or coordinates. The quantity may be selected according to different methods. In one example, the quantity is determined by choosing a random follicular unit among the distribution and rejecting all other proximal follicular units that are not spaced away from the randomly selected follicular unit by at least the selection distance. After making the rejections, the closest remaining follicular unit (or alternatively, another random follicular unit) is selected and the rejection process is repeated. This selection and rejection process may continue until each follicular unit in the distribution either has been selected or has been rejected, or a desired quantity of follicular units is selected in the distribution. The selection and rejection process may proceed linearly (e.g., in step-wise fashion through the distribution) randomly, or according to another selection algorithm. The step 430 may be performed by a processor, control logic hardware, software, manually as described with reference to FIG. 16, or by other components described with reference to FIG. 15.

Once the quantity of follicular units is determined at step 430, the method 400 proceeds to step 440 where it is determined whether the quantity corresponds to a desired quantity or the determined quantity is within a range of a desired quantity based on an acceptable tolerance. The desired quantity may be input by a user, automatically generated by a processor, or determined by a combination of user input and processor analysis. If the quantity is less than or greater than the desired quantity, a different distance is selected as the selection distance at step 450 and the method 400 proceeds to the step 430 and a quantity of follicular units is selected among the distribution of follicular units based on the different distance. If, on the other hand, the determined quantity equals the desired quantity, or within the acceptable tolerance, the method 400 terminates at step 460. Follicular units in the desired quantity may then be selected and harvested, for example, in a hair transplantation procedure. In another example, the desired quantity may then be used to determine or adapt a size of a donor area, or for characterizing other attributes of a donor area. The steps 430, 440, and 450 form a loop or subroutine, which may be repeated multiple times until the selection distance yields the desired quantity of follicular units; however, the first distance may yield the desired quantity in which case no repetition is necessary. One or more of the steps 420-450 may be readily executed by a processor, which is described in further detail with respect to FIG. 15. The steps 420 and 430 may be performed in any order or in parallel (e.g., at the same time).

Figure 5:
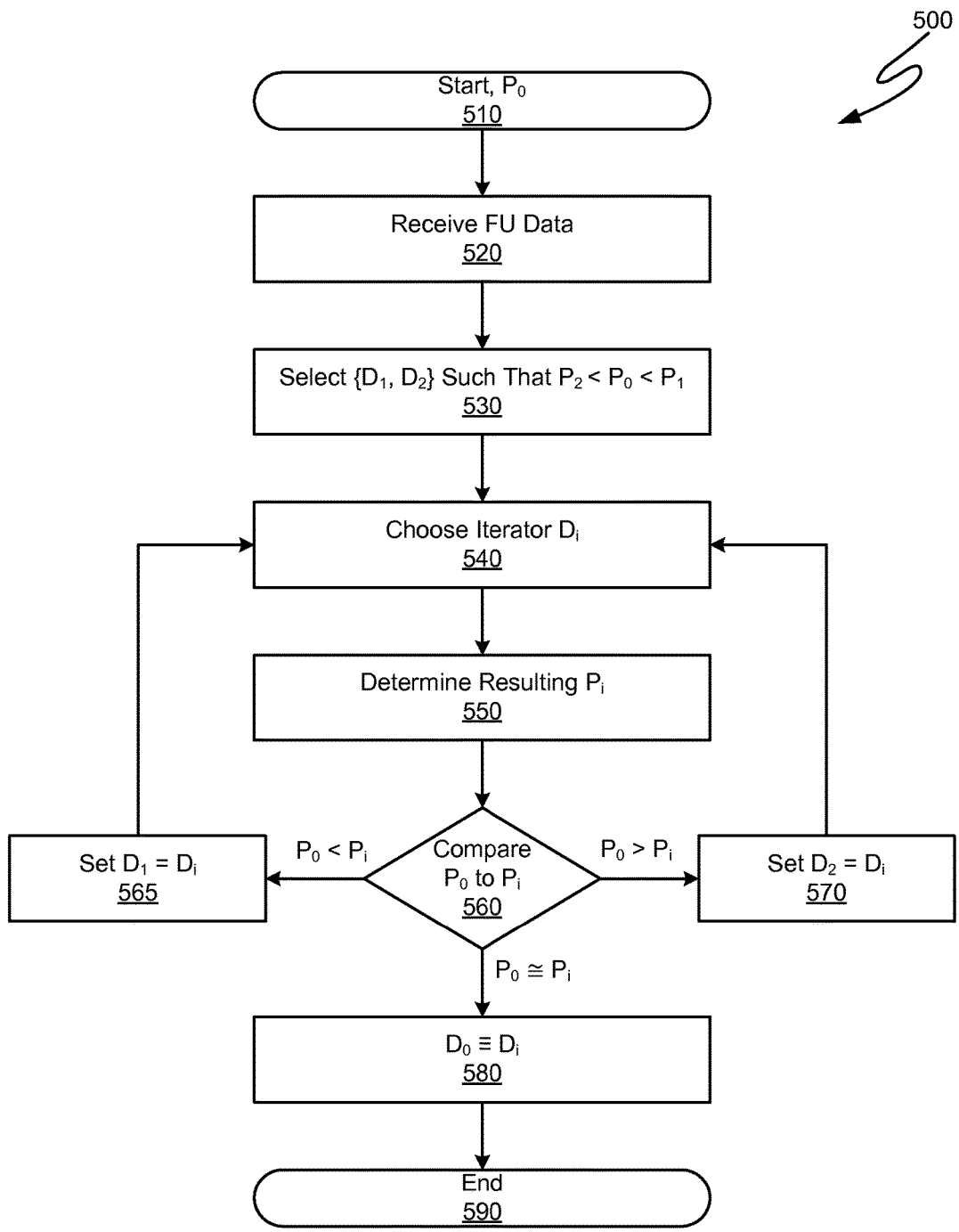
FIG. 5 is a flow diagram of a method of determining a selection distance that yields a desired quantity of follicular units to be selected in a distribution of follicular units, according to another embodiment.

FIG. 5 shows a flow diagram of an example method 500 for determining a minimum interfollicular-unit distance, $D_0$ (or desired distance), between follicular unit to be selected based on a desired quantity of sites, $P_0$. According to the method 500, a desired quantity of follicular units in a given area is used as an input into a binary search routine that identifies a minimum distance between selected follicular units resulting from the desired quantity. In other words, the method 500 identifies a distance that results in a desired quantity of follicular units (e.g., desired percentage of hairs in a given area). Thus, given a pattern of follicular units available on a patient, the method 500 identifies a set of follicular units spaced apart by at least the minimum distance, which yields a desired percentage of follicular units in the pattern. The spaced apart follicular units may then be used for treatment purposes such as harvesting for hair transplantation. Skilled persons will recognize that other distance-related parameters may be identified and that the order of the steps in the method 500 may be rearranged when appropriate and other search routines are contemplated and are within the scope of this disclosure.

Starting at step 510, the desired quantity $P_0$ may be specified in terms of a raw number of sites, a percentage of sites of the distribution, or in terms of densities as described above. For example, with respect to FIG. 2, $P_0$ may be specified as 20%, a density corresponding to 20%, or 228 sites of the 1,140 total follicular units in the donor area 120.

At step 520, follicular unit distribution data reflecting locations of follicular units on a body or skin surface is received. In one example, the distribution data may be in the form of digital image data obtained from one or more cameras as described in U.S. Patent Application Pub. No. 2007/0106306 A1 of Bodduluri et al. ('306 of Bodduluri et al.), entitled "Automated System For Harvesting or Implanting Follicular Units," which is assigned to the assignee of this patent application and is hereby incorporated by reference in its entirety. An example of an image acquisition device is described with reference to FIG. 15. In another example, the distribution data may be a list of coordinate or positional data including locations for the follicular units in a donor area.

At step 530, two different distances $D_1$ and $D_2$ are selected to initiate the method 500, thereby defining the boundaries of a search space. Distance bounds $D_1$ and $D_2$ represent minimum and maximum distances between selected follicular units, and have corresponding quantities of follicular units, $P_1$ and $P_2$. In the method 500, the distance bounds $D_1$ and $D_2$ are selected to satisfy Equation 1:

$$D_1 < D_0 < D_2 \text{ such that } P_2 < P_0 < P_1 \quad \text{Equation 1}$$

Accordingly, $D_1$ is the minimum distance of the search space and $D_2$ is the maximum distance. Skilled persons will recognize that the subscript numerals are arbitrary. In one example, a minimum distance of zero corresponds to 100% of the follicular units in any distribution because each potential site is at least zero distance away from an adjacent potential site. Similarly, a maximum distance exceeding the distance between the two outermost follicular units in a distribution, e.g., 100 mm, results in 0% of the follicular units being selected. Thus, to exhaust the search space, $D_1$ may be selected as 0 mm and $D_2$ may be selected as 100 mm (assuming 100 mm exceeds the distance between the two farthest follicular units in FIGS. 1-3, i.e., the area in FIGS. 1-3 may be 40 mm by 40 mm, for example). Given a desired quantity of follicular units to be harvested, for example, and bounding the search region to between zero and the distance between the two follicular units that are the farthest from each other, the method 500 may search for the distance that results in the desired quantity of follicular units.

As described in further detail below, because the distance bounds $D_1$ and $D_2$ have corresponding quantities $P_1$ and $P_2$, and vice versa, $D_1$ and $D_2$ may be obtained based on a previous selection of $P_1$ and $P_2$ satisfying Equation 1, i.e., $P_2 < P_0 < P_1$.

At step 540, a processor is used to choose an iterator distance, $D_i$, having a value in a range between the first and second distance bounds. The choice of iterator distance may be a selection from a lookup table stored in memory, or a calculation performed by the processor. In one example, the iterator distance may be determined by interpolating, averaging, or bisecting between $D_1$ and $D_2$:

$$D_i = \frac{(D_1 + D_2)}{2} \quad \text{Equation 2}$$

In another example, the iterator distance may be selected from various functions or mathematical models based on attributes and characteristics of a donor area or a donor patient such as age, ethnicity, body surface location, and other characteristics may be used to establish values of the iterator distance.

Next, at step 550, a resulting quantity of follicular units, $P_i$, corresponding to the current calculated iterator distance $D_i$ is determined based on the follicular unit distribution data. The resulting $P_i$ quantity is the percentage (or raw total, or density equivalent) of the follicular units in the distribution data (e.g., the follicular unit distribution 100 in FIGS. 1-3) having an interfollicular-unit distance of at least the current iterator distance $D_i$. The resulting $P_i$ quantity can be determined manually, or by a selection algorithm. As described above, an example selection algorithm selects a follicular unit in the distribution data, disregards any follicular unit within $D_i$ distance, and repeats these two steps until all the follicular units have been selected as sites or have been disregarded. Skilled persons will recognize that computer algorithm techniques may be used to automate the process of determining the distances between selected follicular units to thereby determine $P_i$.

At step 560, a comparison is made between the resulting quantity $P_i$ and the desired quantity $P_0$. At the step 560 it is determined whether the resulting quantity $P_i$ is greater than, less than, or within an acceptable or predetermined tolerance of the desired quantity $P_0$. If the desired quantity $P_0$ is less than the resulting quantity $P_i$ by at least the tolerance, the example method 500 proceeds to step 565. Conversely, if the desired quantity $P_0$ is greater than the resulting quantity $P_i$ by at least the tolerance, the method 500 proceeds to step 570. If the desired quantity $P_0$ and the resulting quantity $P_i$ are approximately equal, i.e., within an acceptable tolerance, the method 500 proceeds to step 580. If $P_0 < P_i$, the lower distance bound $D_1$ may be adapted at step 565 by setting the value, for example, at the value of the current iterator distance $D_i$. If $P_0 > P_i$, the value of the upper bound $D_2$ may be adapted at step 570 to the value of the current iterator distance $D_i$. It is not necessary to set $D_1$ exactly to the value of $D_i$ at step 565 or to set $D_2$ exactly to the value of $D_i$ at step 570. After completion of either of the steps 565 or 570, the method 500 repeats the steps 540-560 (including choosing a new iterator $D_i$, for example, as explained above) until it is determined that the resulting quantity $P_i$ is within the predetermined tolerance of the desired quantity $P_0$. After it is determined at step 560 that the resulting quantity $P_i$ is within the predetermined tolerance of $P_0$, the current value of the iterator distance $D_i$ may be selected as the minimum distance $D_0$ at step 580 and the method terminates at step 590. Step 580 may be omitted in certain embodiments. For example, if the last chosen iterator distance yields the desired quantity $P_0$, the method may terminate at step 590 without performing step 580. The steps in the method 500 may be performed in any order or in parallel (e.g., at the same time).

According to one embodiment, the iterator distance $D_i$ corresponds to the selection distance described in the example 500, such that the steps 530-570 may provide an implementation of the example method 400. According to such embodiment, the first distance of the step 420 may be selected between $D_1$ and $D_2$.

Figure 6:
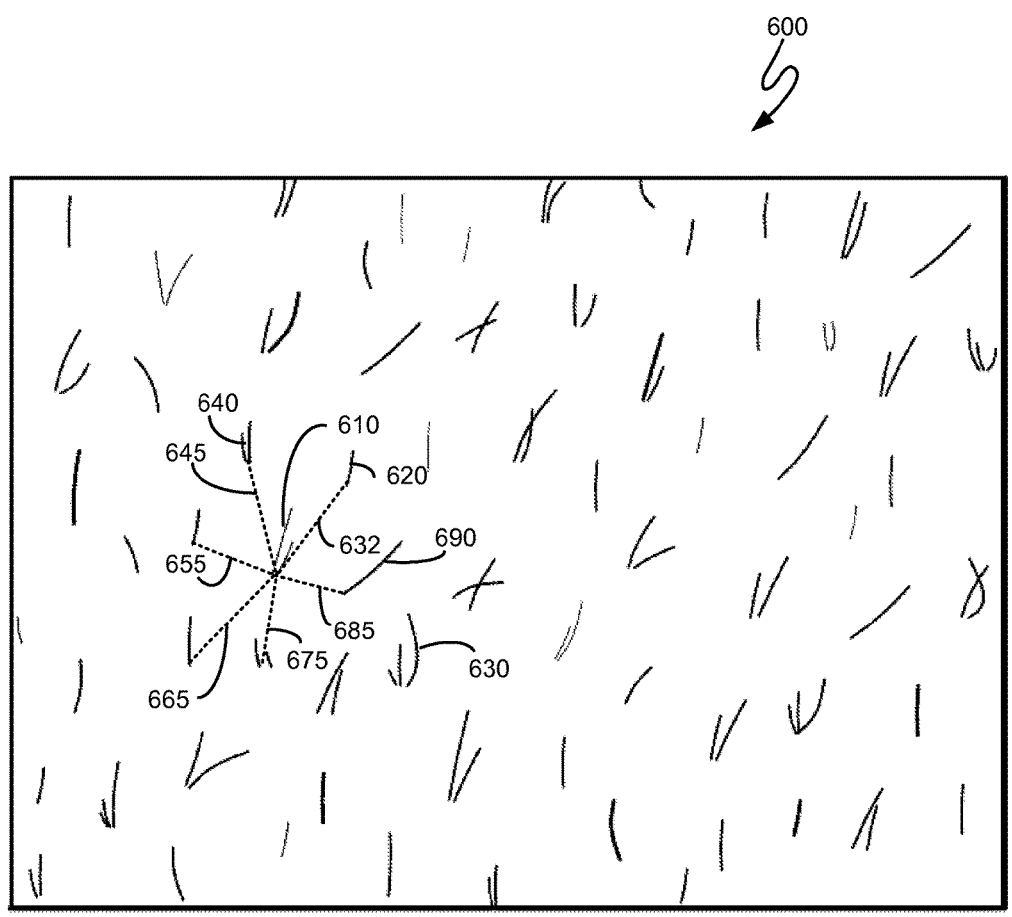
FIG. 6 is a rendering of a human scalp showing various classifications of follicular units and interfollicular-unit distances.

Referring to FIG. 6, a rendering of a human scalp 600 shows a variety of classes (also referred to as "types") of follicular units. For example, the follicular unit 610 includes two hairs and is therefore an F2, while follicular unit 620 is an F1 since it has only a single hair. A follicular unit 630 is an F3 and includes three hairs. The distance between follicular units 610 and 620 is an interfollicular-unit distance 632; the distance between 610 and 640 is an interfollicular-unit distance 645. Interfollicular-unit distances 655, 665, 675, and 685 are also depicted. The distance 685 is the shortest interfollicular-unit distance to follicular unit 610 because a follicular unit 690 is closest to follicular unit 610.

Figure 7:
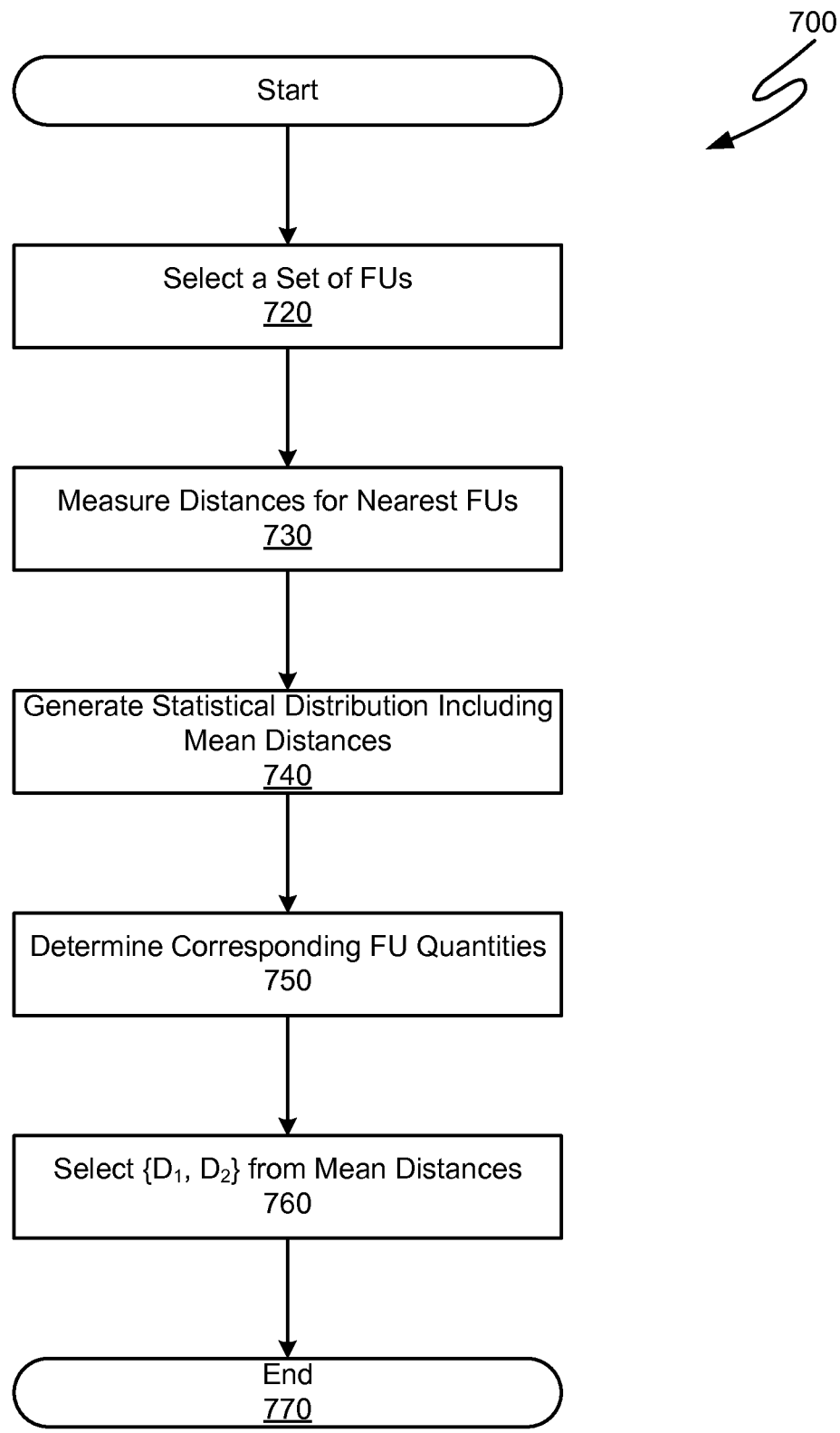
FIG. 7 is a flow diagram of a method of selecting distance bound $D_1$, $D_2$, or both, for example, of FIG. 5 based on a statistical distribution of interfollicular-unit distances, according to one embodiment.

FIG. 7 is a flow diagram showing one example method 700, which may be used to implement step 530 in the method 500 (FIG. 5) to select the distance bounds $D_1$ and $D_2$, based on a statistical distribution of interfollicular-unit distances. In other words, the search region can be reduced by analyzing the distribution of follicular units (e.g., by determining a measure of how close, on average, the follicular units are from one another). At step 720, a sample set of follicular units is selected from follicular unit distribution data exemplified by the donor area 120 (e.g., FIG. 2). The sample set of follicular units may be selected randomly, or selected as a group of follicular units in a particular sub-region of the donor sample 100, or according to another selection method. At step 730, for each individual follicular units in the sample set, distances are measured, for example, to the 20 closest follicular units, such that each individual follicular units in the sample set has corresponding measurements. Fewer or greater measurements may be used as well. For example, assuming follicular unit 610 (FIG. 6) is selected for the sample set, the interfollicular-unit distances 632, 645, 655, 665, 675, and 685 are all measured, along with measurements of 14 other closest follicular units. If the follicular unit 630 were included in the set, it would also have 20 corresponding measurements.

After the sets of measurements are obtained for the sample set, a statistical distribution is generated at step 740. The following example statistical distribution data in Table 1 includes mean distances for the closest follicular units, listed in order from the closest follicular unit to the farthest follicular unit. The standard deviation may also be found or calculated, which provides a measure of how the follicular units are distributed statistically.

TABLE 1

| Order of Closeness | Mean [mm] | Standard Deviation [mm] | FU Selections | Selection % (1,140 FUs) |
|---|---|---|---|---|
| 1 (closest FUs) | 1.061065 | 0.064053 | 799 | 70.1 |
| 2 | 1.142529 | 0.102504 | 613 | 53.8 |
| 3 | 1.251358 | 0.149226 | 497 | 43.6 |
| 4 | 1.395275 | 0.181518 | 405 | 35.5 |
| 5 | 1.561278 | 0.205827 | 333 | 29.2 |
| 6 | 1.739675 | 0.207752 | 289 | 25.4 |
| 7 | 1.920745 | 0.206794 | 250 | 21.9 |
| 8 | 2.066793 | 0.198484 | 225 | 19.7 |
| 9 | 2.183627 | 0.208576 | 202 | 17.7 |
| 10 | 2.289289 | 0.224695 | 187 | 16.4 |
| 11 | 2.388359 | 0.243620 | 163 | 14.3 |
| 12 | 2.485053 | 0.264588 | 159 | 13.9 |
| 13 | 2.581496 | 0.286457 | 142 | 12.5 |
| 14 | 2.676524 | 0.301195 | 135 | 11.8 |
| 15 | 2.771868 | 0.312514 | 124 | 10.9 |
| 16 | 2.868807 | 0.320448 | 121 | 10.6 |
| 17 | 2.962360 | 0.329460 | 117 | 10.3 |
| 18 | 3.056299 | 0.338067 | 109 | 9.6 |
| 19 | 3.141961 | 0.347128 | 107 | 9.4 |
| 20 (farthest FUs) | 3.230040 | 0.363604 | 105 | 9.2 |

Each of the mean distances, when used as a minimum distance between harvests, for example, results in a percentage of harvests as noted in Table 1.

After the mean distances have been generated, a set of derived quantities of follicular units is determined at step 750. The derived quantities may be determined based on the processes described above, e.g., selection and rejection, or other alternative methods. Depending on the desired quantity, $P_0$, a first and second derived quantity may be determined such that $P_2<P_0<P_1$. For example, for the closest follicular units in the distribution 100, having a mean interfollicular-unit distance of 1.061065 mm, corresponds to 799 follicular units, or 70.1% of the 1,140 total follicular units that are spaced apart at least 1.061065 mm. A mean distance of 1.142529 mm results in 613 follicular unit selections, or 53.8%, and so forth. Assuming the desired quantity, $P_0$, of the follicular unit distribution 100 (e.g., FIG. 1) is 684 follicular units (or 60%), $P_2$ may be set as 53.8% and $P_1$ may be set as 70.1%. In other words, given a desired percentage $P_0$ of 60%, Table 1 can be traversed to determine $P_1$ as the next higher percentage relative to $P_0$ (i.e., 70.1%), and $P_2$ as the next lower percentage relative to $P_0$ (i.e., 53.8%), and the corresponding distances $D_1$ and $D_2$. Thus, at step 760, $D_1$ is set as 1.061065 mm and $D_2$ is set as 1.142529 mm and the method 700 terminates at step 770. Skilled persons will recognize that the statistical distribution method 700 potentially reduces the search space when compared to a minimum of zero mm and a maximum of 100 mm as previously described. The steps in the method 700 may be performed in any order or in parallel (e.g., at the same time).

Figure 8:
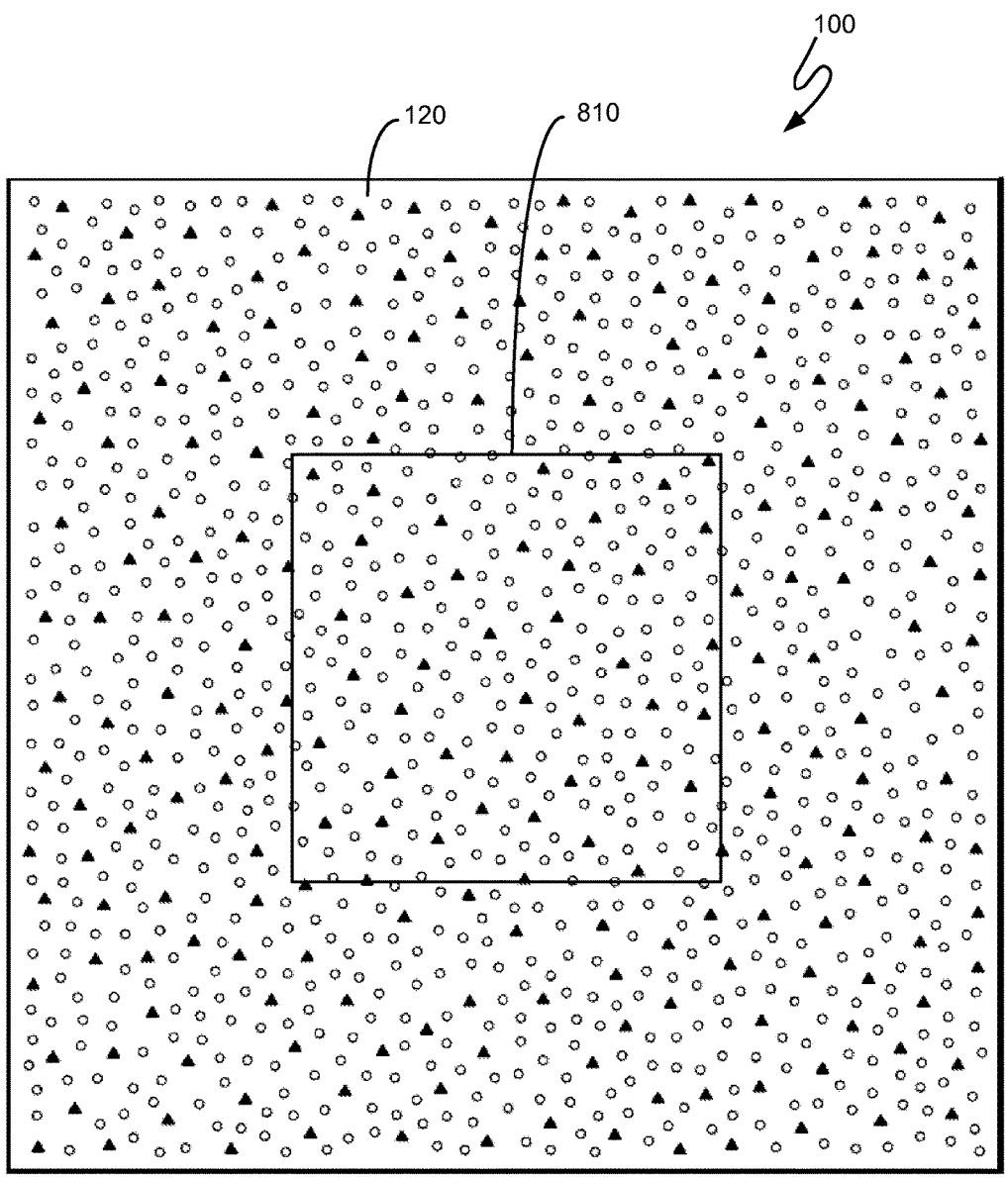
FIG. 8 is a diagram showing an example of a selected sub-region of follicular units in a distribution of follicular units.

FIG. 8 is a diagram showing an example of a selected sub-region 810 of follicular units in the distribution 100. Because follicular units at the border of the distribution 100 have fewer observable adjacent follicular units, an internal border 810 is established such that all the actual closest neighboring follicular units are observable for determining mean distances. Thus, the selected sub-region 810 increases the accuracy of average distances shown in data table (such as Table 1), or for any other methods using a mean distance between follicular units. Skilled persons will recognize that the shape of the border is arbitrary and is intended to facilitate the concept of measuring interfollicular-unit distances from the actual closest neighboring follicular units as opposed to measurements obtained at the edge of the distribution 100 that may or may not be from the closest neighboring follicular units on the body surface 120.

Figure 9:
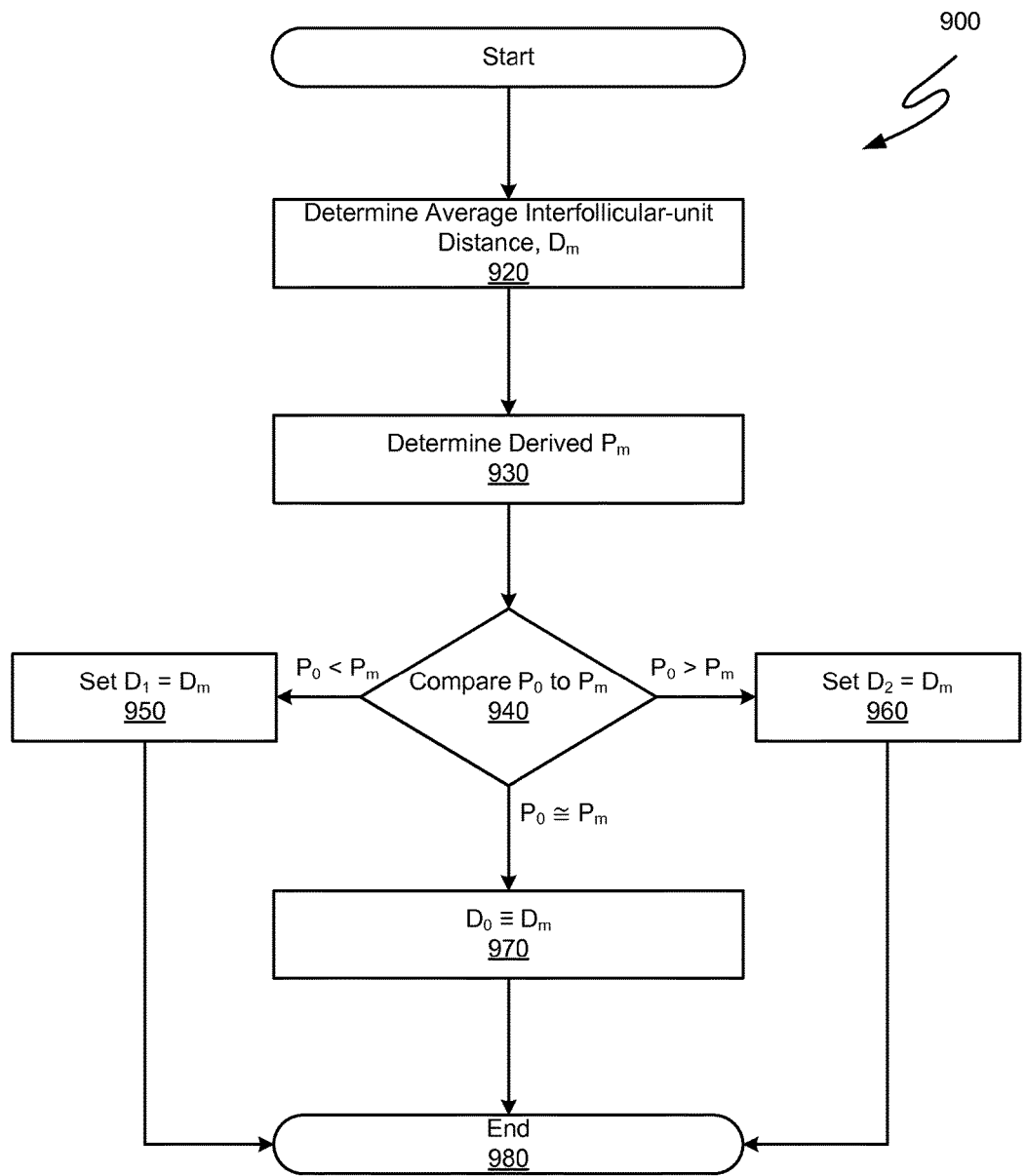
FIG. 9 is a flow diagram of a method of selecting distance bounds $D_1$, $D_2$, or both, based on an average interfollicular-unit distance.

FIG. 9 is a flow diagram showing an alternative method 900, which may be used to implement step 530 in the method 500 (FIG. 5) to select the distance bounds $D_1$ or $D_2$, based on an average interfollicular-unit distance, $D_m$. According to the method 900, the average interfollicular-unit distance $D_m$ is used to limit the search space, and thus reduce the execution time of the method 500, by setting the value of either $D_1$ or $D_2$ as the value of $D_m$.

At step 920, the average interfollicular distance $D_m$ is determined. According to one example, the average interfollicular-unit distance $D_m$ may be derived from the density of follicular units. The density of the follicular units is defined as the number of follicular units in a given region divided by the area of the region. In the example shown in FIGS. 2 and 3, there are 1,140 follicular units in a 16 cm² area, which results in a density of 1,140/16=71.25 FU/cm². The average interfollicular-unit distance can be obtained by first taking the reciprocal of the density, 1/71.25=0.0140 cm² or 1.40 mm², and then taking the square root of the result, $\sqrt{0.0140}$=0.118 cm or 1.18 mm. Another example method for determining an average interfollicular-unit distance $D_m$ based on a characteristic parameter is described below with reference to FIGS. 10-14.

At step 930, a derived quantity, $P_m$, corresponding to the distance $D_m$, is determined. Determining the derived quantity $P_m$ may be performed according to the examples described above for finding $P_i$ in step 550 (FIG. 5), or step 430 (FIG. 4), or by other methods.

At step 940, a comparison is made between the derived quantity $P_m$ and the desired quantity $P_0$ to determine whether the derived quantity $P_m$ is greater than, less than, or within a predetermined tolerance of the desired quantity $P_0$. If the desired quantity $P_0$ is less than the derived quantity $P_m$ by at least the tolerance, the example method 900 proceeds to step 950. Conversely, if the desired quantity $P_0$ is greater than the derived quantity $P_m$ by at least the tolerance, the method 900 proceeds to step 960. If the desired quantity $P_0$ and the derived quantity $P_m$ are approximately equal, i.e., within an acceptable or predetermined tolerance, the method 900 proceeds to step 970. If $P_0<P_m$, the minimum distance $D_1$ may be adapted at step 950 by setting it to the value of the average interfollicular-unit distance, $D_m$. If $P_0>P_m$, the value of the maximum distance $D_2$ may be adapted at step 960 to the value of the average interfollicular-unit distance, $D_m$. The unset distance from either of the steps 950 or 960 may be set as described above, e.g., set by default (0 or 100 mm), set by statistical methods, or by another method. If it is determined at step 940 that the derived quantity $P_m$ is within the predetermined tolerance of $P_0$, the average interfollicular-unit distance $D_m$ may be selected as the desired distance $D_0$ at step 970 and the method terminates at step 980. Step 940 may be repeated for various values or estimates of $P_m$, until $P_0$ approximates a value of $P_m$. Step 970 may be omitted in certain embodiments. For example, to obtain precise values for $D_O$, the method may terminate at step 980 without performing step 970. The example 900 terminates at step 980 upon completion of any of the steps 950, 960, or 970. The steps in the method 900 may be performed in any order or in parallel (e.g., at the same time).

Figure 10:
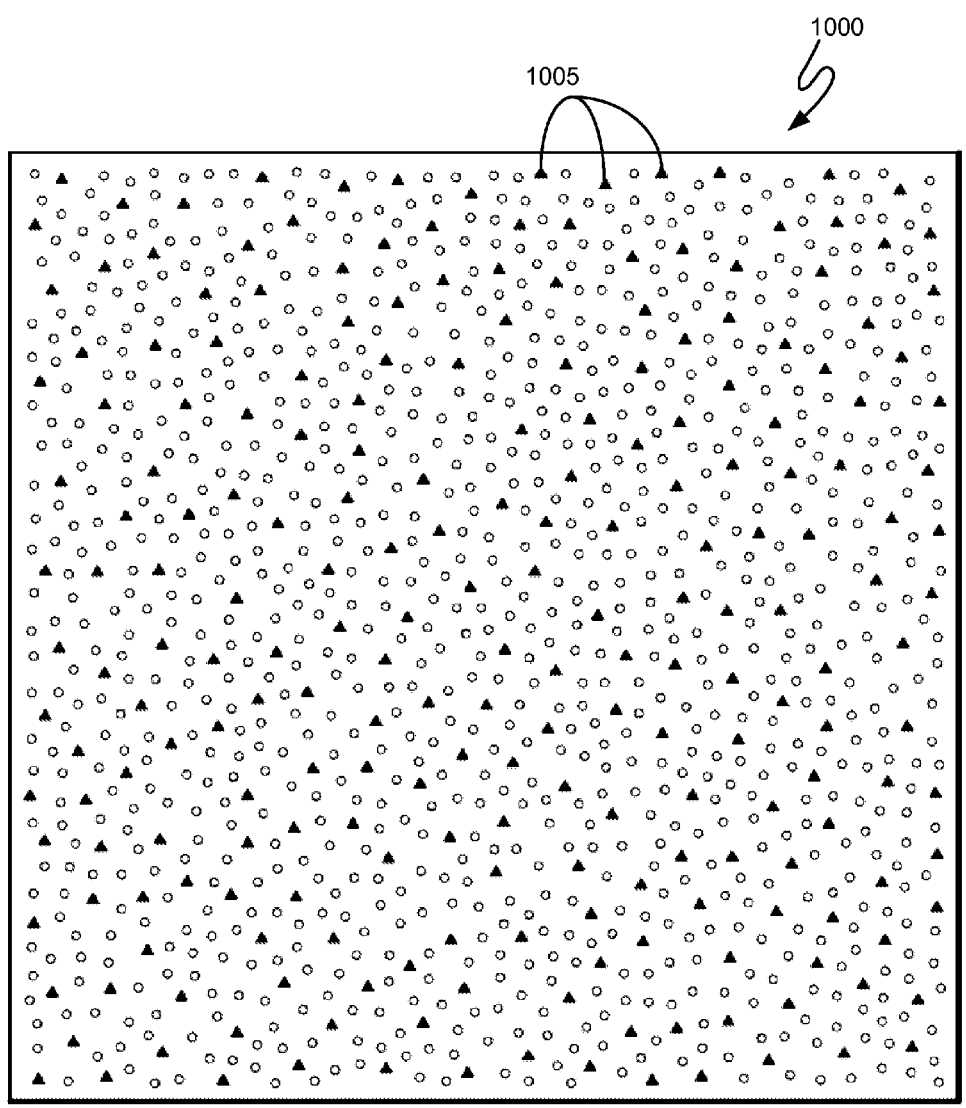
FIG. 10 is a diagram illustrating an example distribution of follicular units on a body surface with missing or unobserved follicular units.

In a perfectly uniform follicular unit distribution, each pair of adjacent follicular units has the same interfollicular-unit distance, regardless of the actual density. Thus, there are six equally distributed follicular units (i.e., grafts) surrounding a given follicular unit in a uniform density distribution. For example, although not perfectly uniform, follicular unit 610 (FIG. 6) is surrounded by six other follicular units. The distances between the center follicular unit 610 to the other follicular unit locations are similar, as are the distances between the adjacent peripheral follicular units. However, if the follicular unit 690 were missing or undetected, the next closest follicular unit would be follicular unit 630, and the distance to the follicular unit 630 would distort the average interfollicular-unit distance of the distribution 600. As shown in FIG. 10, a follicular unit distribution 1000 may include missing follicular units (denoted by triangles 1005) due to previous harvesting procedures or other hair loss causes, or the follicular units 1005 may be undetected for reasons such as occlusion caused by blood, tissue damage, image artifacts, poor lighting, general failure of any automated algorithms, or other discrepancies. A characteristic parameter (described by example as characteristic distance) in this example approximates the average interfollicular-unit distance for a hair pattern and compensates for missing or undetected follicular units 1005. A characteristic parameter in this embodiment disregards the furthest interfollicular-unit distances in calculating an average interfollicular-unit distance. Thus, the characteristic parameter may be determined and used for planning or treatment purposes as described with reference to FIG. 11. The characteristic parameter may also be used as the average interfollicular-unit distance $D_m$ for implementing step 920 of the method 900 (FIG. 9), or as the first distance in the step 420 (FIG. 4), or for other treatment purposes.

Figure 11:
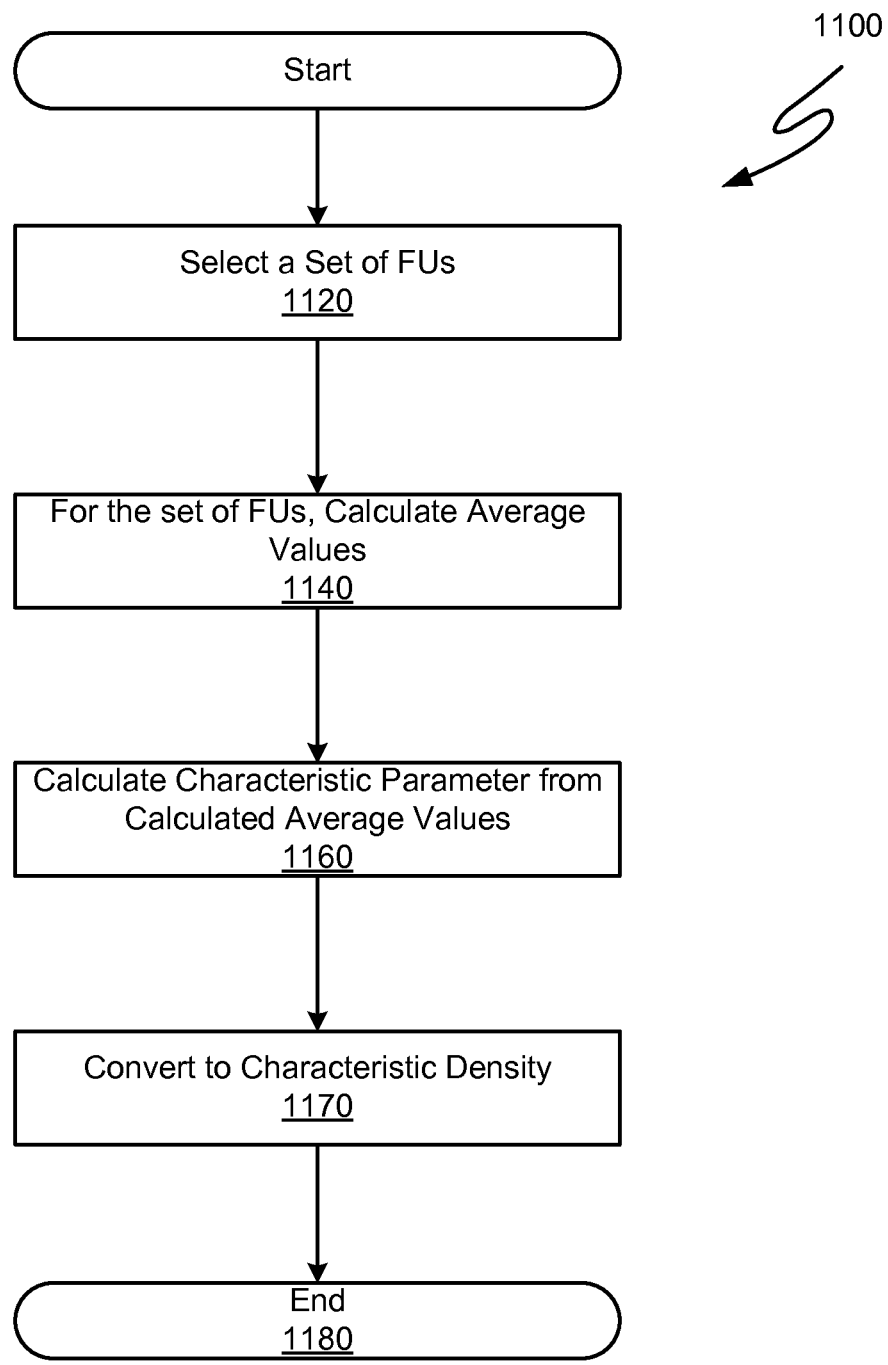
FIG. 11 is a flow diagram of a method for calculating a characteristic distance of a distribution of follicular units, according to one embodiment.

FIG. 11 is a flow diagram for calculating a characteristic parameter (e.g., a distance or distance-related parameter) of a distribution of follicular units. As described below, distances between follicular units may be used to establish the characteristic parameter, i.e., the characteristic distance, although skilled persons will recognize that other distance-related parameters (including area, angles, vectors) as already described above in reference to FIG. 2 may be used to establish a characteristic parameter. For example, vectors may be generated between pairs of follicular units and an average of the dot products of the vectors may be used to establish the characteristic parameter.

Starting at step 1120, a set of follicular units is selected from the distribution 1000. The set of follicular units may be selected manually or automatically, and may be selected in a group, randomly, or according to another selection algorithm as described with reference step 550 (FIG. 5), or step 430 (FIG. 4), or by other methods. A processor or image processor (as described below with reference to FIG. 15) may be used to select the follicular units from the distribution 1000.

According to one example, for each follicular unit in the set, the mean distance of the three closest follicular units is calculated at step 1140 (e.g., three follicular units instead of six follicular units allows for or accommodates missing grafts). Thus, assuming follicular unit 610 is in the set of follicular units, the interfollicular-unit distances 685, 675, and 655 are averaged. If follicular unit 630 were also in the set, the distances to its three closest follicular units are averaged, and so forth for all the follicular units in the set. In other examples there may be more or less than three closest neighboring follicular unit distances that are averaged. For example, the set of closest neighboring follicular units may be the two closest follicular units, or the two median closest distances, or another set of closest neighboring follicular units. In alternative embodiments, other distance-related parameter values are averaged. Software executing on a general-purpose computer or on a dedicated processor as described below may be used to calculate the averages, or the averages may be calculated manually.

At step 1160 an average of the set of mean distances is calculated and the characteristic density is set as the average-of-averages. The characteristic distance may be used as $D_m$ in step 920 of the method 900. At an optional step 1170, the characteristic distance may be converted into a density for further planning or diagnosis purposes. The characteristic distance is converted to a density by squaring the characteristic distance and taking the reciprocal of the result. The desired units may be obtained by dividing the number 100 by the squared characteristic distance. For example, if the characteristic distance is 2 mm, the density (or characteristic density) is 0.25 FU/mm$^2$ or 25 FU/cm$^2$. The characteristic distance or characteristic density may be used for planning purposes or patient consultation, and for example, displayed on a user interface to a doctor or a patient. The example method 1100 terminates at step 1180. The steps in the method 1100 may be performed in any order or in parallel (e.g., at the same time). By obtaining the characteristic distance (or other relevant characteristic parameter), a doctor may determine what the actual average interfollicular-unit distance was, for example, prior to an already previously completed harvesting procedure. In other words, for patients that have already undergone a harvesting procedure, the characteristic distance (or density) may be used to compensate for the missing grafts.

The characteristic distance or density may be also used in an implantation procedure to determine implantation sites consistent with an original characteristic distance or density for a particular patient. For example, a doctor may use the characteristic distance to locate sites to implant follicular units such that the average interfollicular-unit distance between a graft to be implanted and a set of closest surrounding follicular units is approximately equal to the characteristic distance. Thus, the grafts to be implanted may fill in voids and restore the patient's original hair density based on the characteristic distance. The term "original hair density" is defined as hair density that existed prior to some hair loss. "Hair loss" as used herein is not limited to natural hair loss, but encompasses hair loss caused by a previous hair harvesting procedure or baldness conditions such as androgenic alopecia; hair loss as used herein also encompasses existing but simply undetected or unidentified follicles (e.g., due to occlusion, poor lighting or imaging, or general failure of automated algorithms), therefore, while in reality such hairs are not lost and do exist, they are considered lost in a sense of being undetectable.

Figure 12:
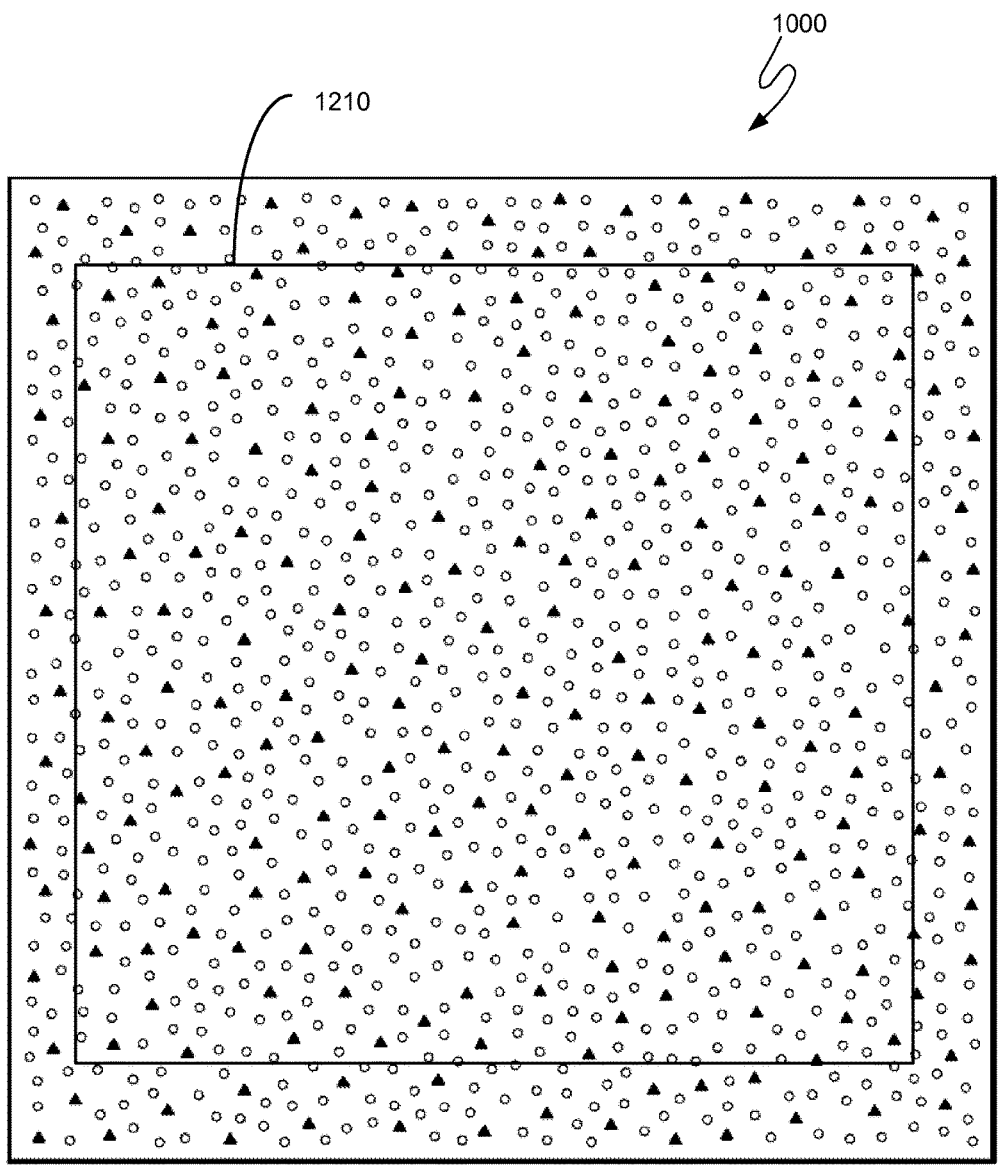
FIG. 12 is a diagram showing an example of a selected sub-region of follicular units in a distribution of follicular units.

FIG. 12 is a diagram showing a selected sub-region of follicular units in the distribution 1000. In one example, at step 1120 (FIG. 11) the set of follicular units are selected to lie within a sub-region 1210 such that the closest follicular units are all observable in the distribution data 1000. As described previously with reference to the sub-region 810 (FIG. 8), the internal border 1210 is established such that all the actual closest neighboring follicular units are observable for determining mean distances.

Figure 13:
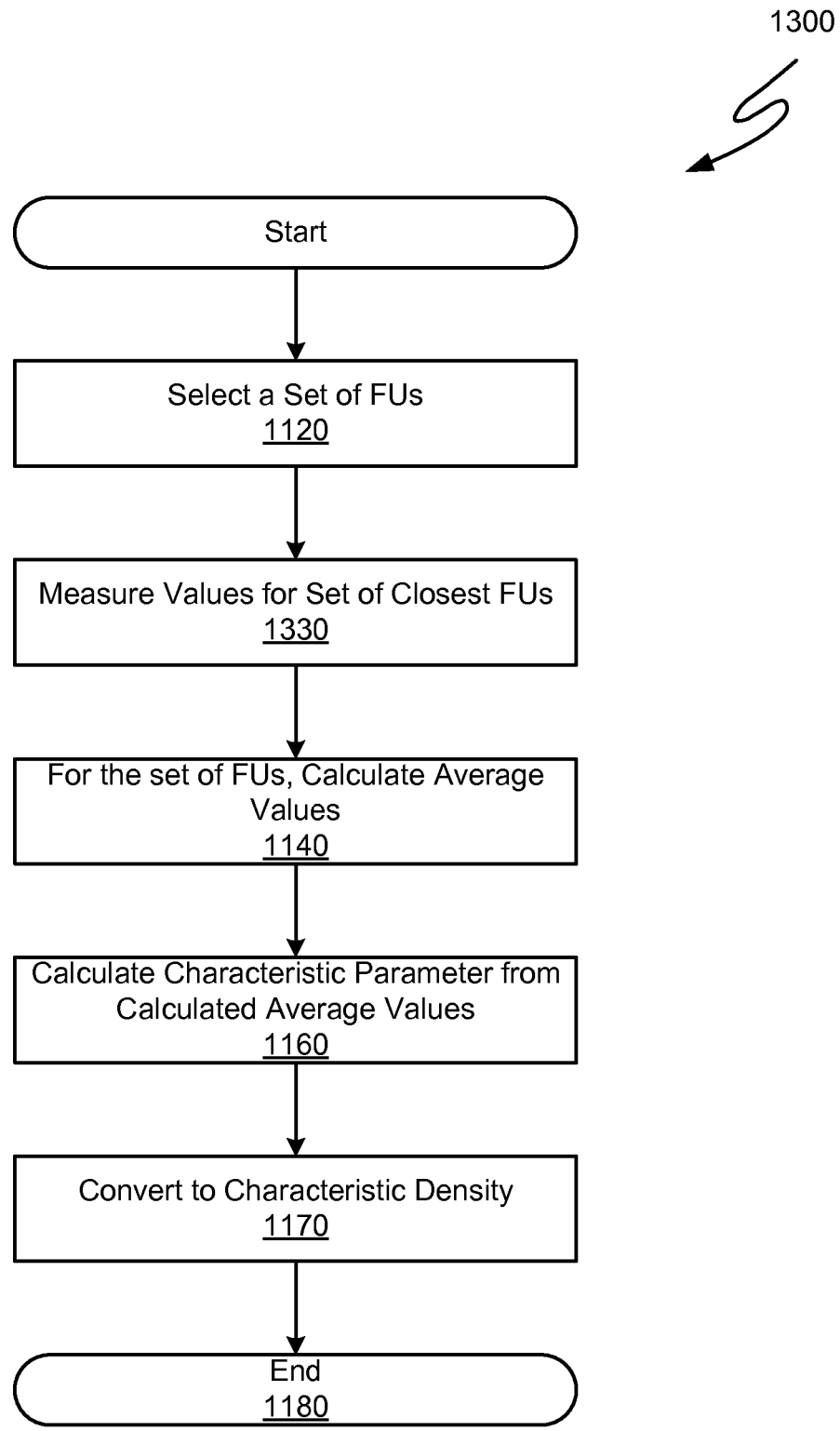
FIG. 13 is a flow diagram of a method for calculating a characteristic distance of a distribution of follicular units, according to another embodiment.

FIG. 13 is a flow diagram of a method 1300 for calculating a characteristic distance of a distribution of follicular units as an average interfollicular-unit distance, according to another embodiment, and includes step 1330. The method 1300 may be substantially similar to the method 1100 (FIG. 11). At step 1330, distances are measured to a set of closest adjacent follicular units for individual follicular units in the set. The distances may be measured manually using measuring tools or a software program with a graphical user interface, measured by a processor or manually from coordinate data, or measured by a processor from image data of a body surface. After measurements are obtained for each follicular unit in the set, the closest distances are sorted and the three closest distances are averaged for each follicular unit in the set at step 1140. For example, assuming the follicular unit 610 (FIG. 6) is selected, the interfollicular-unit distances 685, 675, and 655 are averaged, while the longer interfollicular-unit distances 632, 645, and 665 are ignored.

Figure 14:
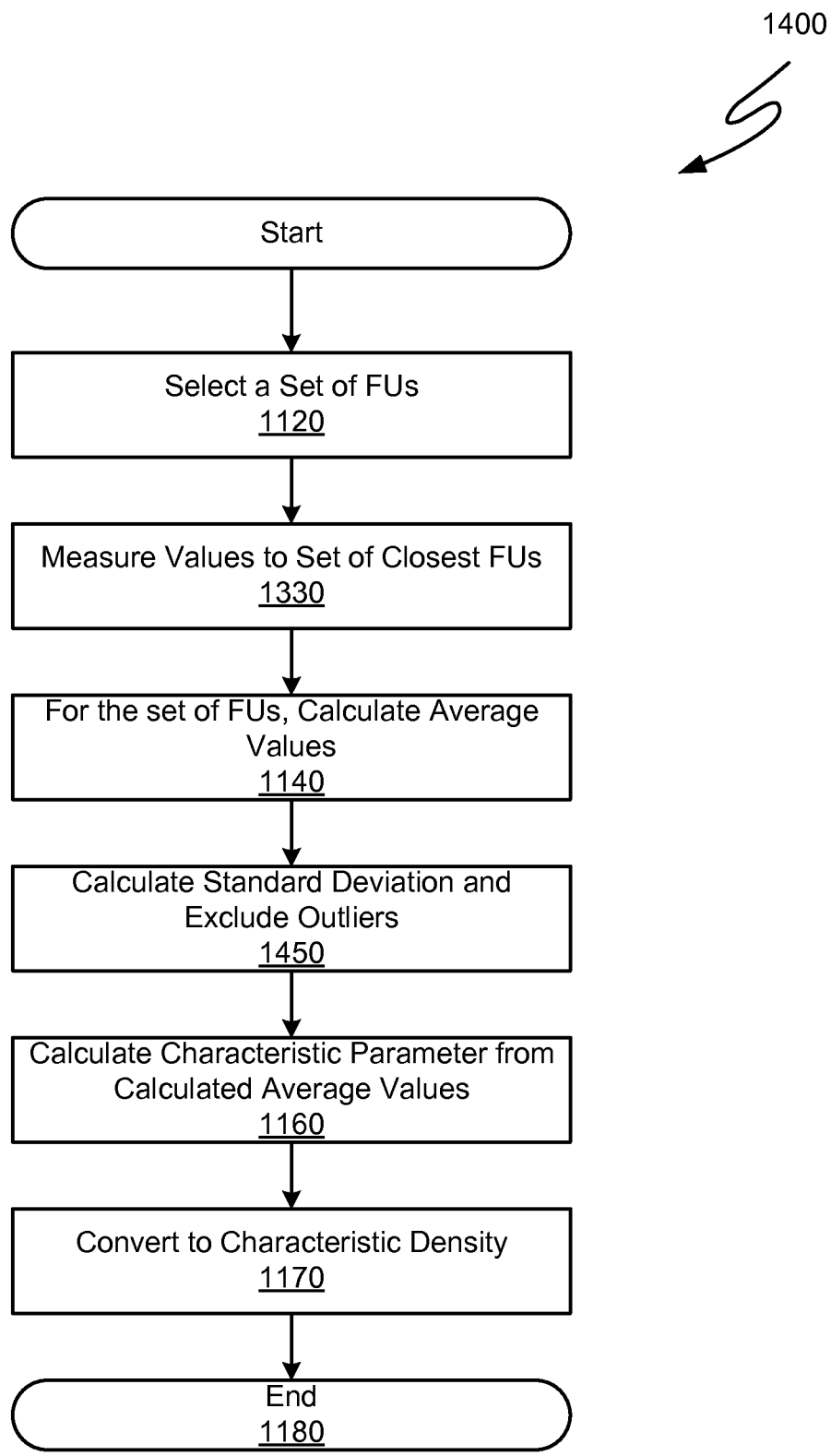
FIG. 14 is a flow diagram, for example, as in FIG. 11, and depicting an optional step of excluding average distances that exceed an acceptable threshold.

FIG. 14 is a method 1400 that is similar to the method 1300. In addition to the method 1300 described above, the method 1400 calculates a standard deviation. Step 1450 is an optional step that calculates a standard deviation for the set of mean distances and excludes any mean distance that exceeds an acceptable threshold. The acceptable threshold is one standard deviation distance according to one example, although skilled persons will recognize that the acceptable threshold may be alternatively specified in terms of distance, or the step 1450 may be skipped altogether.

It should be understood that various concepts described herein may be applied to variety of procedures and applications. For ease of description, the descriptions herein provide examples of hair transplantation procedures. Hair transplantation procedures that are carried out using automated (including robotic) systems or computer-controlled systems have been described, for example, in U.S. Patent Application Pub. No. 2007/0106306 A1 of Bodduluri et al. Although the various examples use follicular units or hairs for purposes of description, it should be apparent that the general understanding of the various concepts discussed are applicable in other contexts. It should be understood that although the examples described herein are suited for use with a robotic system for hair harvesting and/or implanting, the examples may be applied as well to manual hair transplantation using hand-held devices as described with reference to FIG. 16 below, or in other applications.

Figure 15:
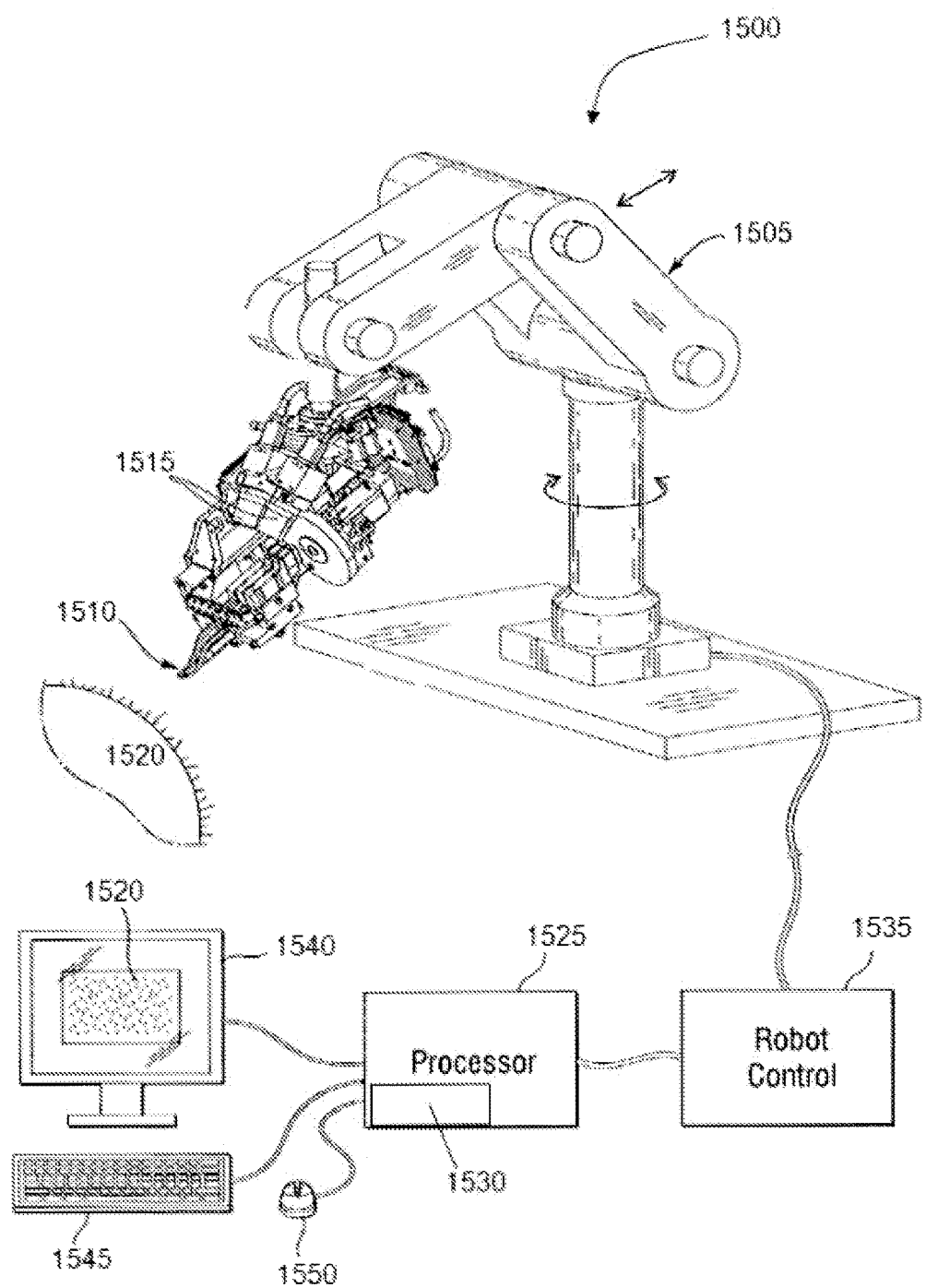
FIG. 15 is a depiction of a robotic hair harvesting system that may be implemented with various embodiments.

FIG. 15 illustrates an example of a robotic system 1500 for harvesting and/or implanting follicular units into a body surface, such as the scalp. The system 1500 includes a robotic arm 1505 to which is coupled a harvesting or implanting tool 1510. Various motors and other movement devices may be incorporated to enable fine movements of an operating tip of the tool 1510 in multiple directions. The robotic system 1500 further includes at least one (and preferably two for stereo vision) image acquisition device 1515 which may be mounted in a fixed position, or coupled (directly or indirectly) to a robotic arm 1505 or other controllable motion device. The operating tip of the tool 1510 is shown positioned over a body surface 1520, in this case a part of a patient's scalp having hair follicles thereon.

The processor 1525 of FIG. 15 comprises an image processor 1530 for processing images obtained from the image acquisition device 1515. The image processor 1530 may be a separate device or it may be incorporated as a part of the processor 1525. The processor 1525 may also instruct the various movement devices of the robotic arm 1505, including the tool 1510, acting, for example, through a controller 1535 as shown in FIG. 15. The controller 1535 may be operatively coupled to the robotic arm 1505 and configured to control the motion of the robotic arm 1505, including the motion based on the images or data acquired by the image acquisition device 1515. Alternatively, controller 1535 may be incorporated as a part of the processor 1525, so that all processing and controls of all movements of all the various tools, the robotic arm 1505 and any other moveable parts of the assembly, including those based on the images or data acquired by the image acquisition device 1515, are concentrated in one place. The system 1500 may further include any number of input or output devices such as a monitor 1540, keyboard 1545, and mouse 1550. A magnified image of the body surface 1520 can be seen on the imaging display or monitor 1540. In addition, the system 1500 may comprise other tools, devices and components useful in harvesting and/or implantation of the hair follicles, or in hair treatment planning. The system 1500 further comprises an interface (not shown) adapted to receive image data. Various parts of the system allow an operator to monitor conditions and provide instructions, as needed. The processor 1525 may interact with the imaging device 1515 via the interface. The interface may include hardware ports, cables, leads, and other data transmission means, or it may comprise a computer program.

Some non-limiting examples of an image acquisition device 1515 shown in FIG. 15 include one or more cameras, such as any commercially available cameras. An example image acquisition or imaging device may be held, for example, by a robotic arm, or by any other mechanism or means. Of course, various image acquisition devices or a combination of several devices could be used with any of the examples described herein. The image acquisition device 1515 may comprise a device that takes still images, it can also comprise a device capable of real time imaging (e.g., webcam capable of continuously streaming real time or video information), and/or it could also have a video recording capability (such as a camcorder). While stereo or multi-view imaging devices are useful in the present disclosure, it is not necessary to employ such geometries or configurations, and the present disclosure is not so limited. Likewise, the image acquisition device 1515 may be digital or analog. For example, the image acquisition device could be an analog TV camera that acquires an initial image, which is then processed into a digital image (for example, via an analog-to-digital device like a commercial-off-the-shelf frame grabber) for further use in the methods of the present disclosure. The image acquisition device 1515 may be coupled to the processor to control the imaging operation and to process image data.

Typically, the processor 1525 operates as a data processing device, for example, it may be incorporated into a computer. The processor 1525 may include a central processing unit or parallel processor, and input/output interface, a memory with a program, wherein all the components may be connected by a bus. Further, the computer may include an input device, a display, and may also include one or more secondary storage devices. The bus may be internal to the computer and may include an adapter for receiving a keyboard or input device or may include external connections.

The processor 1525 may execute a program that may be configured to include predetermined operations and methods, such as one or more of the methods 400, 500, 700, 900, 1100, 1300, 1400. The processor may access the memory in which may be stored at least one sequence of code instructions comprising the program for performing predetermined operations. The memory and the program may be located within the computer or may be located external thereto. By way of example, and not limitation, a suitable image processor 1530 may be a digital processing system which includes one or more processors or other type of device. For example, a processor and/or an image processor may be a controller or any type of personal computer (PC). Alternatively, the processor may comprise an Application Specific Integrated Circuit (ASIC) or Field Programmable Gate Array (FPGA). It will be understood by skilled persons that the processor and/or the image processor for use with the present disclosure is programmed and configured to perform various known image processing techniques, for example, segmentation, edge detection, object recognition and selection. These techniques are generally known and do not need to be separately described here.

The methods described herein may be implemented on various general or specific purpose computing systems. In certain embodiments, the methods of the present application may be implemented on a specifically configured personal computer or workstation. In other embodiments, the methods may be implemented on a general-purpose workstation, including one connected to a network. Alternatively or additionally, the methods of the disclosure may be, at least partially, implemented on a card for a network device or a general-purpose computing device. The processor 1525 and/or image processor 1530 may also include memory, storage devices, and other components generally known in the art and, therefore, they do not need to be described in detail here. The image processor 1530 could be used in conjunction with various manual, partially automated and fully automated (including robotic) hair transplantation systems and devices, including but not limited to systems for hair harvesting, implantation or transplantation.

The imaging display device 1540 may comprise a high resolution computer monitor which may optionally be a touch screen. The imaging display may allow images, such as video or still images, to be readable and for follicular units, and parts thereof, to be visualized. Alternatively, the imaging display device 1540 can be other touch sensitive devices, including tablet, pocket PC, and other plasma screens. The touch screen may be used to display, monitor and modify the parameters of the hair transplantation procedure directly through the image display device.

Methods, apparatus and systems consistent with the disclosure may be carried out by providing a modification interface, or user modification interface, including clickable icons, selection buttons in a menu, dialog box, or a roll-down window of an interface that may be provided to feed into the computer. According to another embodiment, the imaging display device 1540 may display the selection window and a stylus or keyboard for displaying monitoring, modifying or entering a selection, such as selection parameters or characteristic parameters (e.g. distances, density, etc.), for example, directly on the display itself. According to one embodiment, commands may be input via the modification interface through a programmable stylus, keyboard, mouse, speech processing system, laser pointer, touch screen, remote control device, or other input mechanism. Alternatively, the modification interface may comprise a dedicated piece of hardware. In some embodiments, the selections or adjustment made through the modification interface may be executed by code instructions that may be executed on a processor, for example, the computer processor.

Figure 16:
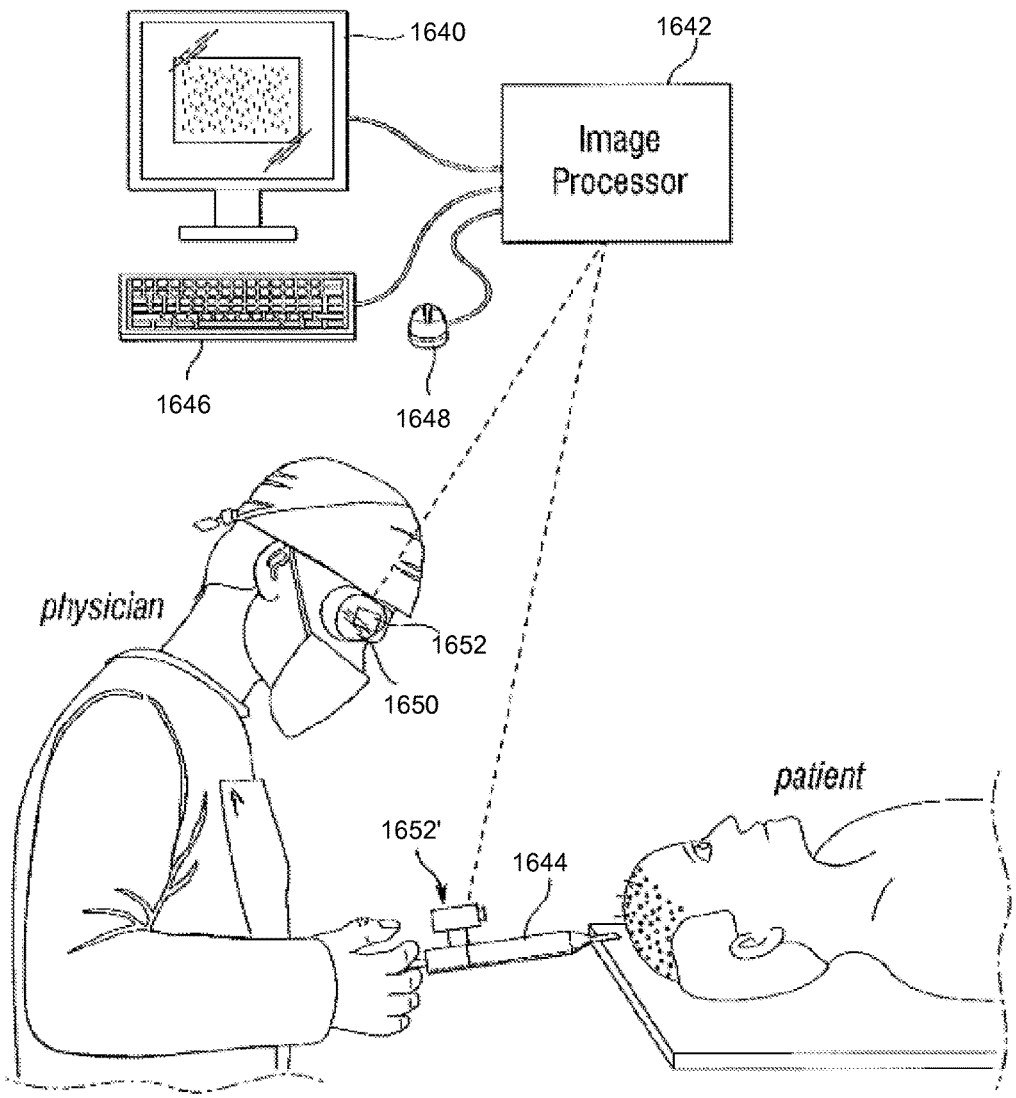
FIG. 16 is a depiction of a non-robotic hair harvesting system that may be implemented with various embodiments.

According to another aspect, follicular unit selections may be also implemented in a procedure conducted by a doctor using some hand-held tool for hair harvesting. One such implementation is shown as an example in FIG. 16. In this embodiment, a physician is conducting a manual operation on the patient using a hand-held harvesting tool 1644 and wearing glasses 1650 that have high-magnification lupes. An image acquisition device 1652, such as one or more cameras, may be attached to the glasses. The camera(s) may have viewfinders such that when attached to the glasses it allows the physician to view exactly what the cameras are imaging. Alternatively, the cameras 1652' may be attached to the hand-held instrument or tool that physician is using for hair harvesting. In some additional embodiments, it may be a stand-alone image acquisition device. FIG. 16 shows two of the alternative examples of the image acquisition device as 1652 (on the glasses) and 1652' on the tool 1644. The image processor, such as the computer 1642, may execute various methods described herein. The monitor 1640 displays the highlighted follicular unit or units, as well as other useful data/statistics, for example, an exact count of hair, approximate density, follicular unit types, characteristic density, or other attributes. Guided by the information displayed on the monitor, the physician may select the next follicular unit for harvesting.

Embodiments may be implemented using computer software developed in various programming languages. Embodiments may be provided as a computer program product including a nontransitory machine-readable storage medium having stored thereon instructions (in compressed or uncompressed form) that may be used to program a computer (or other electronic device) to perform processes or methods described herein. The machine-readable storage medium may include, but is not limited to, hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of media/machine-readable medium suitable for storing electronic instructions. Further, embodiments may also be provided as a computer program product including a transitory machine-readable signal (in compressed or uncompressed form). Examples of machine-readable signals, whether modulated using a carrier or not, include, but are not limited to, signals that a computer system or machine hosting or running a computer program can be configured to access, including signals downloaded through the Internet or other networks. For example, distribution of software may be via CD-ROM or via Internet download.

Software programs that execute the methods and systems described herein may include a separate program code including a set of instructions for performing a desired operation or may include a plurality of modules that perform such sub-operations of an operation, or may be part of a single module of a larger program providing the operation. The modular construction facilitates adding, deleting, updating and/or amending the modules therein and/or features within the modules. The program may receive unique identifier information and/or additional information and may access, for example, a storage device having data associated with the unique identifier information and/or additional information.

The terms and descriptions used above are set forth by way of illustration only and are not meant as limitations. Skilled persons will recognize that many variations can be made to the details of the above-described embodiments without departing from the underlying principles of the disclosure. The scope of the invention should therefore be determined only by the following claims and their equivalents.

The invention claimed is:

1. A method of calculating a characteristic parameter of follicular units from follicular unit distribution data, the method comprising:
   for a set of selected follicular units, calculating, with a processor, an average value of a parameter between a selected follicular unit and a set of closest neighboring follicular units to establish a set of average values; and
   calculating, with the processor, the characteristic parameter as the average of the set of average values.

2. The method according to claim 1, wherein the follicular unit distribution data comprises an image of a body surface or follicular unit coordinate data obtained by physical measurement, digital image processing, or a combination of physical measurement and digital image processing.

3. The method according to claim 1, further comprising: converting the characteristic parameter into a density to establish a characteristic density of the follicular units.

4. The method according to claim 1, further comprising: determining a density of individual hair follicles.

5. The method according to claim 1, wherein the step of calculating the average value of the parameter between the selected follicular unit and the set of closest neighboring follicular units is performed for a sub-set of the selected follicular units corresponding to a sub-set of the follicular unit distribution data.

6. The method according to claim 1, further comprising:
   calculating a standard deviation of the set of average values; and
   excluding from the step of calculating the characteristic parameter any average value exceeding an acceptable threshold value.

7. The method according to claim 1, wherein the set of closest neighboring follicular units comprises at least three closest neighboring follicular units.

8. The method according to claim 1, further comprising: harvesting follicular units based on the characteristic parameter.

9. The method according to claim 1, further comprising: determining implantation sites based on the characteristic parameter such that follicular units to be implanted and existing follicular units approximate an original hair density.

10. The method according to claim 1, further comprising:
    selecting the characteristic parameter as a selection parameter to be used for selecting follicular units in a distribution of follicular units;
    determining a quantity of follicular units to be selected in the distribution of follicular units based on a value of the selection parameter; and
    iteratively selecting a different value as the value of the selection parameter and repeating the determining step until the value of the selection parameter yields a desired quantity of follicular units to be selected in the distribution of follicular units.

11. The method according to claim 1, wherein the characteristic parameter is a distance or distance-related.

12. A method of calculating a characteristic parameter of follicular units from follicular unit distribution data, the method comprising:
    for a set of selected follicular units in a distribution of follicular units, calculating, with a processor, an average value of a parameter between a selected follicular unit and a set of closest neighboring follicular units to establish a set of average values;
    calculating an average of the set of average values to establish a characteristic parameter of follicular units; and
    selecting, based on the characteristic parameter or an original density derived therefrom, implantation sites on a body surface or follicular units to be harvested from the distribution of follicular units.

13. A system for calculating a characteristic parameter of follicular units from follicular unit distribution date, the system comprising:
    an interface configured to receive follicular unit distribution data reflecting locations of follicular units on a body surface;
    one or more modules comprising instructions for calculating, for a set of selected follicular units, an average value of a parameter between a selected follicular unit and a set of closest neighboring follicular units to establish a set of average values; and
    one or more modules comprising instructions for calculating a characteristic parameter as the average of the set of average values.

14. The system according to claim 13, further comprising instructions for converting the characteristic parameter into a density to establish a characteristic density of the follicular units, and for calculating a standard deviation parameter of the set of average values and excluding any average value exceeding an acceptable threshold value when calculating the characteristic parameter.

15. The system of claim 13, further comprising an image acquisition device for acquiring images or data.

16. The system according to claim 13, further comprising instructions for:
    selecting the characteristic parameter as a selection parameter to be used for selecting follicular units in a distribution of follicular units, determining a quantity of follicular units to be selected in the distribution of follicular units based on a value of a selection parameter, and iteratively selecting a different value as the value of the selection parameter and repeating the determining step until the value of the selection parameter yields the desired quantity of follicular units to be selected in the distribution of the follicular units.

17. The system of claim 16, wherein the value of the selection parameter further compensates for missing or undetected follicular units.

18. The system of claim 16, wherein the desired quantity of follicular units comprises a desired harvest quantity of follicular units or a desired reserve quantity of follicular units to be retained in a donor area after a harvesting procedure.

19. The system of claim 16, the system further comprising instructions for using the selection parameter which yields the desired quantity of follicular units to determine implantation sites.

20. The system of claim 13, further comprising instructions to select follicular units that are substantially uniformly distributed in the distribution of follicular units.

* * * * *